(12) United States Patent
Iliopoulos et al.

(10) Patent No.: US 11,952,362 B2
(45) Date of Patent: Apr. 9, 2024

(54) COMPOSITIONS AND METHODS FOR TREATING EPIGENETIC DISEASE

(71) Applicant: The Regents of the University of California, Oakland, CA (US)

(72) Inventors: Dimitrios Iliopoulos, Los Angeles, CA (US); Michael E. Jung, Los Angeles, CA (US); Jonghoon Kim, Los Angeles, CA (US); Jill M. Hoffman, Sherman Oaks, CA (US); Iordanes Karagiannides, North Hollywood, CA (US)

(73) Assignee: The Regents of the University of California, Oakland, CA (US)

( * ) Notice: Subject to any disclaimer, the term of this patent is extended or adjusted under 35 U.S.C. 154(b) by 77 days.

(21) Appl. No.: 17/262,081

(22) PCT Filed: Jul. 22, 2019

(86) PCT No.: PCT/US2019/042746
§ 371 (c)(1),
(2) Date: Jan. 21, 2021

(87) PCT Pub. No.: WO2020/023333
PCT Pub. Date: Jan. 30, 2020

(65) Prior Publication Data
US 2021/0309634 A1    Oct. 7, 2021

Related U.S. Application Data

(60) Provisional application No. 62/702,183, filed on Jul. 23, 2018.

(51) Int. Cl.
*C07D 401/06* (2006.01)
*A61P 1/04* (2006.01)
*C07D 409/06* (2006.01)

(52) U.S. Cl.
CPC .............. *C07D 401/06* (2013.01); *A61P 1/04* (2018.01); *C07D 409/06* (2013.01)

(58) Field of Classification Search
CPC .............. C07D 401/06; C07D 409/06; C07D 207/337; C07D 403/06; C07D 405/06; A61P 1/04; A61P 19/02; A61P 29/00; A61P 35/00; A61P 37/06; A61K 31/40; A61K 31/4025; A61K 31/4439; A61K 31/497; A61K 31/7068; A61K 45/06
See application file for complete search history.

(56) References Cited

FOREIGN PATENT DOCUMENTS

| CN | 103524372 A | 1/2014 |
|---|---|---|
| WO | WO-2017/009373 A1 | 1/2017 |
| WO | WO-2017/029514 A1 | 2/2017 |
| WO | WO-2020/023333 A1 | 1/2020 |

OTHER PUBLICATIONS

Extended European Search Report for EP Application No. 19839880.2 dated May 4, 2022.
International Preliminary Report on Patentability for International Application No. PCT/US2019/042746 dated Feb. 4, 2021.
Li et al., "HDACs and HDAC Inhibitors in Cancer Development and Therapy," Cold Spring Harbor Perspectives in Medicine, 6(10): p. a026831 pp. 1-34 (2016).
Di Giorgio et al., "Selective class IIa HDAC inhibitors: myth or reality," Cell Mol Life Sci 72(1):73-86 (2015).
Fleming et al., "Improved synthesis and structural reassignment of MC1568: a class IIa selective HDAC inhibitor," J Med Chem 57(3):1132-1135 (2014).
International Search Report and Written Opinion for International Application No. PCT/US2019/042746 dated Nov. 5, 2019.
Mai et al., "Class II (IIa)-selective histone deacetylase inhibitors. 1. Synthesis and biological evaluation of novel (aryloxopropenyl) pyrrolyl hydroxyamides," J Med Chem 48(9):3344-3353 (2005).
Panella et al., "MC1568 inhibits HDAC6/8 activity and influenza A virus replication in lung epithelial cells: role of Hsp90 acetylation," Fut Med Chem 8(17):2017-2031 (2016).
Ragno et al., "Class II-selective histone deacetylase inhibitors. Part 2: alignment-independent GRIND 3-D QSAR, homology and docking studies," Euro J Med Chem 43(3):621-632 (2008).
Schotterl, "Modulation of immune responses by histone deacetylase inhibitors," Crit Revs Oncogen 20(1-2):139-154 (2015).
Zhan et al., "Medicinal chemistry insights into novel HDAC inhibitors: an updated patent review (2012-2016)," Recent Patents on Anti-Cancer Drug Discovery 12(1):16-34 (2017).

*Primary Examiner* — Robert H Havlin
(74) *Attorney, Agent, or Firm* — Foley Hoag LLP; David P. Halstead; Alexander J. Chatterley

(57) ABSTRACT

The present disclosure provides compounds and compositions capable of treating cancer or an autoimmune disease, such as Crohn's disease, and methods of use thereof.

11 Claims, 14 Drawing Sheets

COMPOSITIONS AND METHODS FOR TREATING EPIGENETIC DISEASE

CROSS REFERENCE TO RELATED APPLICATIONS

This application is the U.S. National Stage of International Application No. PCT/US19/42746, filed on Jul. 22, 2019, which claims the benefit of, and priority to, U.S. Provisional Patent Application No. 62/702,183, filed Jul. 23, 2018, the disclosure of which is incorporated herein by reference in its entirety.

BACKGROUND

Epigenetic alterations have been involved in the pathogenesis of cancer and auto-immune diseases, including Crohn's Disease, Ulcerative Colitis, Lupus and Rheumatoid Arthritis. Histone deacetylases (HDACs) are enzymes that catalyze the removal of acetyl functional groups from the lysine residues of both histone and non-histone proteins. HDAC enzymes are divided into four different classes: Class I (HDAC 1,2,3,8), Class II (HDAC4,5,6,7,9,10), Class III (SIRT1-7) and Class IV (HDAC11). HDACs 4, 5, 7, & 9 consist the Class IIA. There is an unmet need to develop HDAC inhibitors that are selective for certain HDAC isoforms.

SUMMARY OF THE INVENTION

In certain aspects, the present disclosure provides a compound of formula I, or a pharmaceutically acceptable salt thereof:

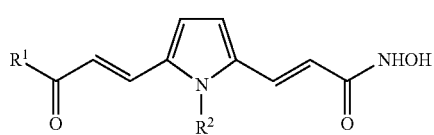

(I)

wherein:
$R^1$ is aryl or heteroaryl; and
$R^2$ is alkyl.

In certain aspects, the present disclosure provides methods of treating a disease selected from a cancer or an autoimmune disease in a subject, comprising administering to the subject a compound or composition as disclosed herein.

DETAILED DESCRIPTION OF THE INVENTION

Figure 1A:
FIGS. 1A-1D show treatment with MJK-006 resulted in significant differences in colon length, clinical and histological scoring during TNBS colitis as compared to vehicle-treated mice.

The present disclosure provides small molecule HDAC inhibitors, aiming to target specific isoforms of the HDAC Class IIA members.

In certain aspects, the present disclosure provides a compound of formula I, or a pharmaceutically acceptable salt thereof:

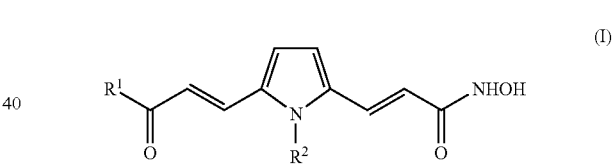

(I)

wherein:
$R^1$ is aryl or heteroaryl; and
$R^2$ is alkyl.

In certain embodiments, the compound is not

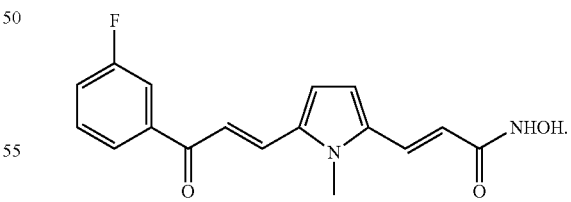

In certain embodiments, $R^1$ is 6-membered aryl or 5- to 6-membered heteroaryl.

In certain such embodiments, $R^1$ is phenyl optionally substituted, e.g., at the 2-position, with alkoxy, such as methoxy, or halo, such as chloro.

In other such embodiments, $R^1$ is pyrrolyl and is optionally substituted at the N-position with alkyl, such as methyl.

In yet other such embodiments, $R^1$ is pyridinyl, pyrazinyl, thiophenyl, or furanyl. In some such embodiments, $R^1$ is pyridinyl, such as pyridin-2-yl, pyridin-3-yl, or pyridin-4-yl. In some other such embodiments, $R^1$ is thiophenyl, such as thiophen-3-yl or thiophen-2-yl.

In certain embodiments, $R^2$ is methyl.

In certain embodiments, the present disclosure provides a pharmaceutical composition comprising a compound as disclosed herein and a pharmaceutically acceptable excipient.

Exemplary compounds of the present disclosure are shown below.

MJK001

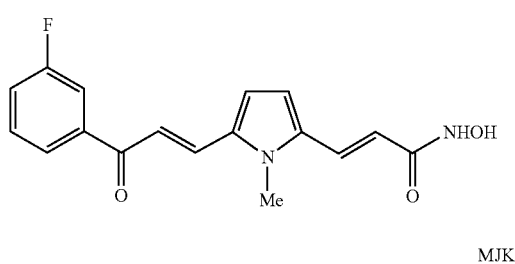

MJK002

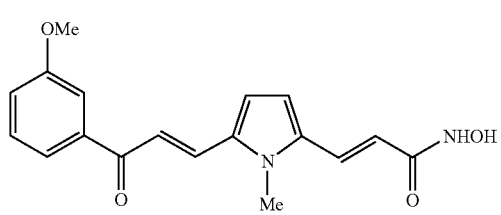

MJK003

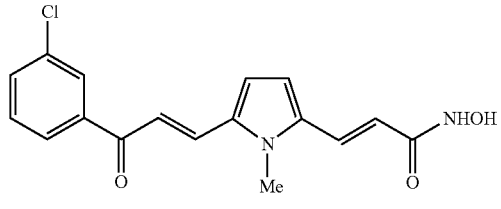

MJK004

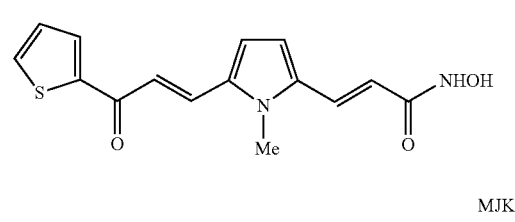

MJK005

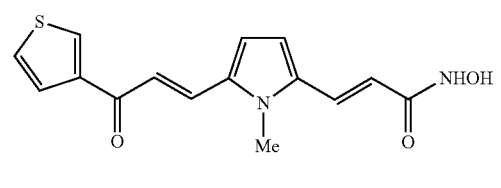

MJK006

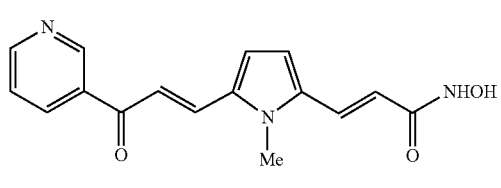

MJK007

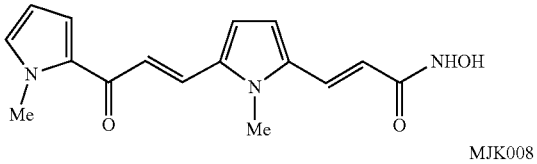

MJK008

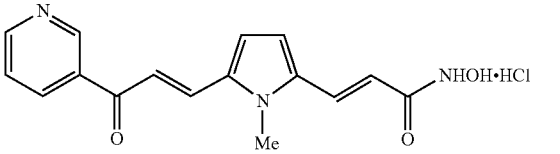

MJK009

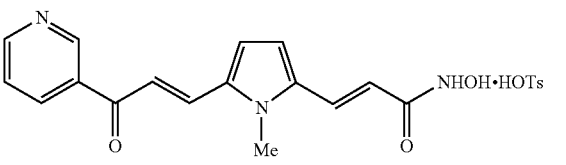

MJK010

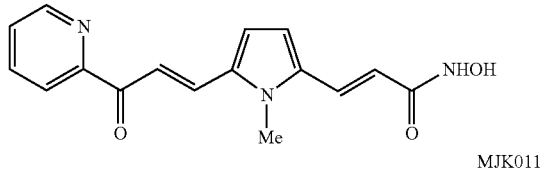

MJK011

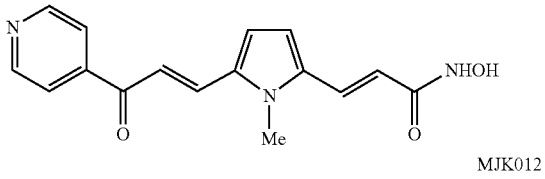

MJK012

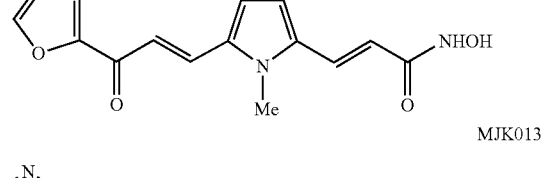

MJK013

The compounds of the present disclosure have increased specificity for the HDAC9 or HDAC4 isoforms. MJK008 and MJK006 are effective in blocking inflammation in vitro and in vivo through regulation of HDAC9. MJK004 is highly efficient in blocking bladder cancer cell growth through regulation of HDAC4. MJK006 and MJK008, based on in vitro and in vivo studies for specificity against HDAC9, can be used as therapeutics for Crohn's Disease and other auto-immune diseases. MJK004 can be used as a therapeutic against bladder cancer in combination with chemotherapy.

In certain aspects, the present disclosure provides a method of inhibiting an HDAC enzyme, such as an HDAC Class IIA enzyme, preferably a HDAC9 or HDAC4 isoform, in a subject, comprising administering to the subject a compound or composition as disclosed herein. In certain such embodiments, $R^1$ is pyridinyl, such as pyridin-2-yl, pyridin-3-yl, or pyridin-4-yl. In other such embodiments, $R^1$ is thiophenyl, such as thiophen-3-yl or thiophen-2-yl.

In certain aspects, the present disclosure provides methods of treating a disease selected from a cancer or an autoimmune disease in a subject, comprising administering to the subject a compound or composition as disclosed herein.

In certain embodiments wherein the disease is a cancer, such as bladder cancer, $R^1$ is thiophenyl, such as thiophen-3-yl or thiophen-2-yl. In preferred such embodiments, the compound is

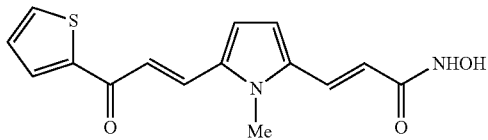

or a pharmaceutically acceptable salt thereof.

In certain embodiments wherein the disease is an autoimmune disease, such as ulcerative colitis, Crohn's disease, lupus or rheumatoid arthritis, $R^1$ is pyridinyl, such as pyridin-2-yl, pyridin-3-yl, or pyridin-4-yl. In preferred such embodiments, the compound is

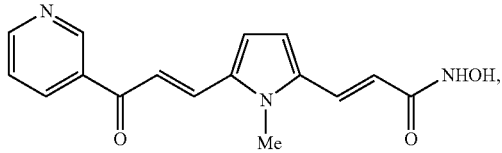

or a pharmaceutically acceptable salt thereof.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, parenterally (for example, intravenously), orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, l-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "acetal" is art-recognized and may be represented by the general formula

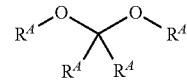

wherein each $R^A$ independently represents hydrogen or a hydrocarbyl, such as alkyl, or any occurrence of $R^A$ taken together with another and the intervening atom(s) complete a carbocycle or heterocycle having from 4 to 8 atoms in the ring structure.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

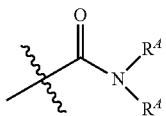

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

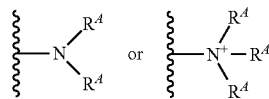

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "boron" as used herein with respect to a substituent on an organic compound, is art-recognized and refers to a group —$B(R^A)_2$, wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

The term "boronic ester" or "boronate ester" as used herein is art-recognized and refers to a group —$B(OR^A)_2$, wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

The term "carbamate" is art-recognized and refers to a group

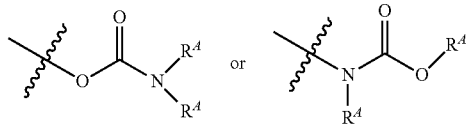

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^A$, wherein $R^A$ represents a hydrocarbyl group.

The term "carboxy", as used herein, refers to a group represented by the formula —$CO_2H$.

The term "diazo", as used herein, refers to a group represented by the formula =N=N.

The term "disulfide" is art-recognized and refers to a group —S—S—$R^A$, wherein $R^A$ represents a hydrocarbyl group.

The term "enol ester", as used herein, refers to a group —C(O)O—C($R^A$)=C($R^A$)$_2$ wherein $R^A$ represents a hydrocarbyl group.

The term "ester", as used herein, refers to a group —C(O)O$R^A$ wherein $R^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "orthoester" as used herein is art-recognized and refers to a group —C(OR$^A$)$_3$, wherein each R$^A$ independently represents hydrogen or a hydrocarbyl, such as alkyl, or any occurrence of R$^A$ taken together with another and the intervening atom(s) complete a heterocycle having from 4 to 8 atoms in the ring structure.

The term "phosphoester", as used herein, refers to a group —P(O$_2$)OH.

The term "phosphodiester", as used herein, refers to a group —P(O$_2$)OR$^A$ wherein R$^A$ represents a hydrocarbyl group.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "selenide", as used herein, is equivalent to an ether, wherein the oxygen is replaced with a selenium.

The term "selenoxide" is art-recognized and refers to the group —Se(O)—R$^A$, wherein R$^A$ represents a hydrocarbyl.

The term "siloxane" is art-recognized and refers to a group with an Si—O—Si linkage, such as the group —Si(R$^A$)$_2$—O—Si—(R$^A$)$_3$, wherein each R$^A$ independently represents hydrogen or hydrocarbyl, such as alkyl, or both R$^A$ taken together with the intervening atom(s) complete a heterocycle having from 4 to 8 atoms in the ring structure.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from C$_{1-6}$ alkyl, C$_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

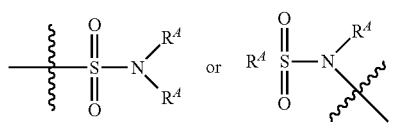

wherein each R$^A$ independently represents hydrogen or hydrocarbyl, such as alkyl, or both R$^A$ taken together with the intervening atom(s) complete a heterocycle having from 4 to 8 atoms in the ring structure.

The term "sulfoxide" is art-recognized and refers to the group —S(O)—R$^A$, wherein R$^A$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^A$, wherein R$^A$ represents a hydrocarbyl.

The term "thioalkyl", as used herein, refers to an alkyl group substituted with a thiol group.

The term "thioester", as used herein, refers to a group —C(O)SR$^A$ or —SC(O)R$^A$ wherein R$^A$ represents a hydrocarbyl.

The term "thioether", as used herein, is equivalent to an ether, wherein the oxygen is replaced with a sulfur.

The term "urea" is art-recognized and may be represented by the general formula

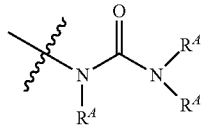

wherein each R$^A$ independently represents hydrogen or a hydrocarbyl, such as alkyl, or any occurrence of R$^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1: Synthesis of Exemplary Compounds of the Disclosure

Preparation of Ethyl (E)-3-(5-formyl-1-methyl-1H-pyrrol-2-yl)-2-propenoate (3)

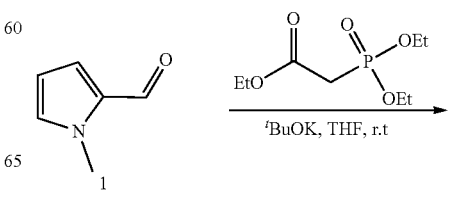

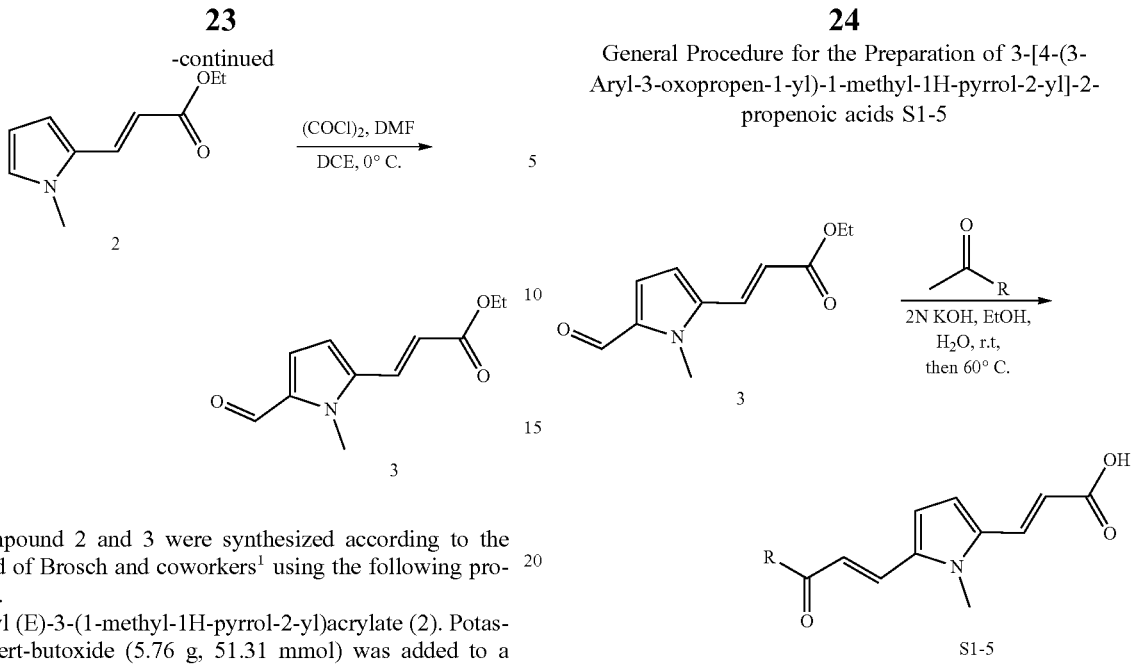

Compound 2 and 3 were synthesized according to the method of Brosch and coworkers[1] using the following procedure.

Ethyl (E)-3-(1-methyl-1H-pyrrol-2-yl)acrylate (2). Potassium tert-butoxide (5.76 g, 51.31 mmol) was added to a stirring solution of triethyl phosphonacetate (8.73 ml, 43.98 mmol) in tetrahydrofuran (THF, 350.0 mL) and the mixture was stirred at 0° C. for 30 min. A solution of N-methyl-2-pyrrolecarboxaldehyde 1 (4.00 g, 36.65 mmol) in THF (350.0 mL) was added to the resultant solution and the mixture was stirred at 22° C. for 48 h. The mixture was quenched with saturated $NH_4Cl$ (aq) and extracted twice with ethyl acetate (EtOAc). The combined organic layer was dried over anhydrous $MgSO_4$ and the filtrate was condensed under reduced pressure, followed by silica-gel flash column chromatography to afford compound 2 (5.55 g, 30.97 mmol, 84%, $R_f$=0.30 (EtOAc/Hexane=1:4)) as a yellow oil.

$^1$H NMR (400 MHz, $CDCl_3$) δ 7.59 (d, J=15.9 Hz, 1H), 6.73 (br t, J=2.1 Hz, 1H), 6.65 (dd, J=3.9, 1.2 Hz, 1H), 6.17-6.12 (m, 2H), 4.23 (q, J=7.2 Hz, 2H), 3.70 (s, 3H), 1.32 (t, J=7.2 Hz, 3H). $^{13}$C NMR (100 MHz, $CDCl_3$) δ 167.9, 132.3, 129.4, 127.0, 112.8, 112.0, 109.4, 60.2, 34.5, 14.5.

Ethyl (E)-3-(5-formyl-1-methyl-1H-pyrrol-2-yl)-2-propenoate (3). A solution of oxalyl chloride (2.62 mL, 30.97 mol) in DCE (100.0 mL) was added to a cooled (0° C.) solution of N,N-dimethylformamide (2.39 mL, 30.97 mmol) in 1,2-dichloroethane (DCE, 100.0 mL) dropwise over 15 min and the mixture was stirred at 0° C. for 15 min. A solution of ethyl (E)-3-(1-methyl-1H-pyrrol-2-yl)acrylate (2) (5.55 g, 30.97 mol) in DCE (100.0 mL) was added to the resultant suspension at 0° C. After being stirred at 0° C. for 1 h, the mixture was quenched with cold water and adjusted to pH 7 using 2 N NaOH (aq). The organic layer was separated and then the aqueous layer was extracted twice with dichloromethane (DCM, 50.0 mL). The combined organic solutions were washed with 1N HCl, dried over anhydrous $MgSO_4$ and the filtrate was condensed under reduced pressure followed by recrystallization from methanol to afford the desired product ethyl (E)-3-(5-formyl-1-methyl-1H-pyrrol-2-yl)-2-propenoate (3) (4.56 g, 21.99 mmol, 71%, $R_f$=0.25 (EtOAc/Hexane=1:4)) as a white solid.

$^1$H NMR (400 MHz, $CDCl_3$) δ 9.54 (s, 1H), 7.57 (d, J=15.6 Hz, 1H), 6.87 (dd, J=4.4, 0.7 Hz, 1H), 6.62 (br d, J=4.4 Hz, 1H), 6.37 (d, J=15.9 Hz, 1H), 4.23 (q, J=7.1 Hz, 2H), 4.00 (s, 3H), 1.30 (t, J=7.1 Hz, 3H). $^{13}$C NMR (100 MHz, $CDCl_3$) δ 180.0, 166.4, 138.0, 134.1, 130.4, 124.1, 120.7, 110.9, 60.8, 32.5, 14.3.

General Procedure for the Preparation of 3-[4-(3-Aryl-3-oxopropen-1-yl)-1-methyl-1H-pyrrol-2-yl]-2-propenoic acids S1-5

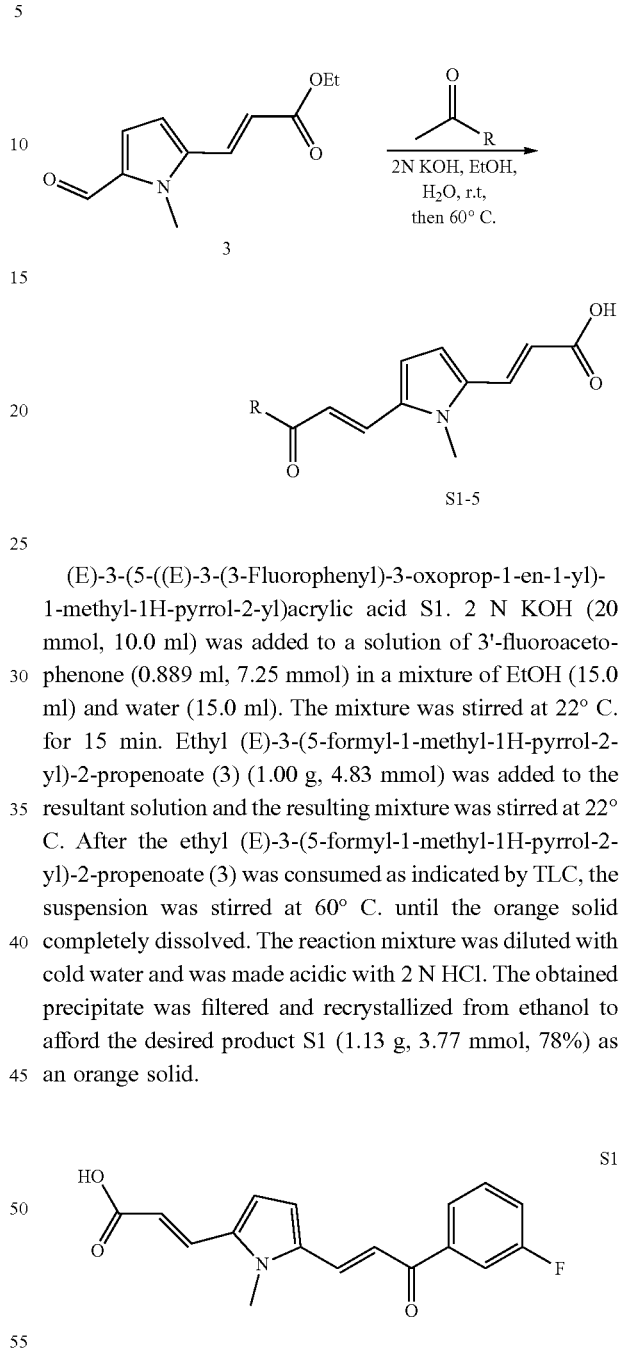

(E)-3-(5-((E)-3-(3-Fluorophenyl)-3-oxoprop-1-en-1-yl)-1-methyl-1H-pyrrol-2-yl)acrylic acid S1. 2 N KOH (20 mmol, 10.0 ml) was added to a solution of 3'-fluoroacetophenone (0.889 ml, 7.25 mmol) in a mixture of EtOH (15.0 ml) and water (15.0 ml). The mixture was stirred at 22° C. for 15 min. Ethyl (E)-3-(5-formyl-1-methyl-1H-pyrrol-2-yl)-2-propenoate (3) (1.00 g, 4.83 mmol) was added to the resultant solution and the resulting mixture was stirred at 22° C. After the ethyl (E)-3-(5-formyl-1-methyl-1H-pyrrol-2-yl)-2-propenoate (3) was consumed as indicated by TLC, the suspension was stirred at 60° C. until the orange solid completely dissolved. The reaction mixture was diluted with cold water and was made acidic with 2 N HCl. The obtained precipitate was filtered and recrystallized from ethanol to afford the desired product S1 (1.13 g, 3.77 mmol, 78%) as an orange solid.

$^1$H NMR (400 MHz, DMSO-$d_6$) δ 12.24 (br s, 1H), 7.92 (d, J=7.6 Hz, 1H), 7.85 (br d, J=9.8 Hz, 1H), 7.74 (d, J=15.2 Hz, 1H), 7.65 (d, J=15.2 Hz, 1H), 7.59-7.51 (m, 2H), 7.44 (td, J=8.4, 2.4 Hz, 1H), 7.21 (d, J=4.2 Hz, 1H), 6.93 (d, J=4.2 Hz, 1H), 6.32 (d, J=15.7 Hz, 1H), 3.72 (s, 3H). $^{13}$C NMR (100 MHz, DMSO-$d_6$) δ 186.9 (d, $^4J_{C,F}$=2.3 Hz), 167.7, 162.4 (d, $^1J_{C,F}$=243.6 Hz), 140.3 (d, $^3J_{C,F}$=6.2 Hz), 134.3, 133.8, 131.7, 131.1, 130.9 (d, $^3J_{C,F}$=7.7 Hz), 124.4 (d, $^4J_{C,F}$=3.1 Hz), 119.6 (d, $^2J_{C,F}$=21.4 Hz), 118.1, 117.1, 114.7 (d, $^2J_{C,F}$=22.2 Hz), 114.1, 112.6, 30.5.

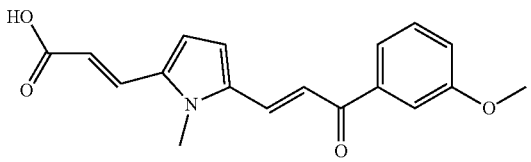

(E)-3-(5-((E)-3-(3-Methoxyphenyl)-3-oxoprop-1-en-1-yl)-1-methyl-1H-pyrrol-2-yl)acrylic acid S2

This compound was synthesized according to the synthetic procedure for the preparation of S1 from 3'-methoxyacetophenone (0.200 ml, 1.46 mmol) and ethyl (E)-3-(5-formyl-1-methyl-1H-pyrrol-2-yl)-2-propenoate (3) (200 mg, 0.97 mmol) in 71% yield (214 mg, 0.69 mmol) as an orange solid. $^1$H NMR (400 MHz, DMSO-$d_6$) δ 12.27 (br s, 1H), 7.77-7.66 (m, 3H), 7.59-7.55 (m, 2H), 7.47 (t, J=7.9 Hz, 1H), 7.23-7.19 (m, 2H), 6.96 (d, J=4.4 Hz, 1H), 6.35 (d, J=15.6 Hz, 1H), 3.84 (s, 3H), 3.77 (s, 3H). $^{13}$C NMR (100 MHz, DMSO-$d_6$) δ 187.9, 167.8, 159.5, 139.4, 134.1, 133.9, 131.2, 131.1, 129.8, 120.7, 118.7, 116.9, 113.8, 112.9, 112.6, 55.3, 30.5 (one low-field carbon not observed).

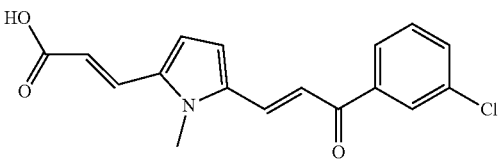

(E)-3-(5-((E)-3-(3-Chlorophenyl)-3-oxoprop-1-en-1-yl)-1-methyl-1H-pyrrol-2-yl)acrylic acid S3

This compound was synthesized according to the synthetic procedure for the preparation of S1 from 3'-chloroacetophenone (0.190 ml, 1.46 mmol) and ethyl (E)-3-(5-formyl-1-methyl-1H-pyrrol-2-yl)-2-propenoate (3) (200 mg, 0.97 mmol) in 65% yield (199 mg, 0.63 mmol) as an orange-red solid. $^1$H NMR (400 MHz, DMSO-$d_6$) δ 12.29 (br s, 1H), 8.12 (s, 1H), 8.06 (d, J=7.6 Hz, 1H), 7.77 (d, J=15.2 Hz, 1H), 7.72-7.68 (m, 2H), 7.59-7.55 (m, 2H), 7.26 (d, J=4.2 Hz, 1H), 6.97 (d, J=4.2 Hz, 1H), 6.36 (d, J=15.7 Hz, 1H), 3.77 (s, 3H). $^{13}$C NMR (100 MHz, DMSO-$d_6$) δ 186.8, 167.7, 139.8, 134.4, 133.81, 133.77, 132.5, 131.8, 131.1, 130.7, 127.8, 126.9, 118.0, 117.2, 114.2, 112.6, 30.5.

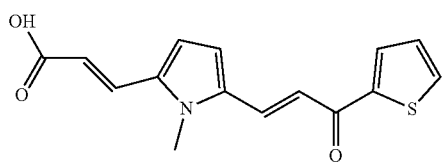

(E)-3-(1-Methyl-5-((E)-3-oxo-3-(thiophen-2-yl)prop-1-en-1-yl)-1H-pyrrol-2-yl)acrylic acid S4

This compound was synthesized according to the synthetic procedure for the preparation of S1 from 2-acetylthiophene (184 mg, 1.46 mmol) and ethyl (E)-3-(5-formyl-1H-pyrrol-2-yl)-2-propenoate (3) (330 mg, 1.59 mmol) in 66% yield (300 mg, 1.04 mmol) as an orange solid. $^1$H NMR (400 MHz, DMSO-$d_6$) δ 12.25 (br s, 1H), 8.21 (d, J=2.9 Hz, 1H), 8.00 (d, J=4.9 Hz, 1H), 7.71 (d, J=14.9 Hz, 1H), 7.64-7.55 (m, 2H), 7.29 (t, J=4.4 Hz, 1H), 7.19 (d, J=4.4 Hz, 1H), 6.97 (d, J=4.4 Hz, 1H), 6.35 (d, J=15.6 Hz, 1H), 3.76 (s, 3H). $^{13}$C NMR (100 MHz, DMSO-$d_6$) δ 180.9, 167.8, 146.0, 134.9, 134.1, 133.7, 132.7, 131.1, 130.3, 128.8, 118.7, 116.9, 113.6, 112.6, 30.5.

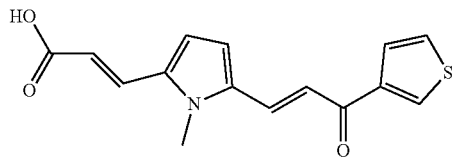

(E)-3-(1-Methyl-5-((E)-3-oxo-3-(thiophen-3-yl)prop-1-en-1-yl)-1H-pyrrol-2-yl)acrylic acid S5

This compound was synthesized according to the synthetic procedure for the preparation of S1 from 3-acetylthiophene and ethyl (E)-3-(5-formyl-1-methyl-1H-pyrrol-2-yl)-2-propenoate (3) (400 mg, 1.93 mmol) in 72% yield (400 mg, 1.39 mmol) as an orange solid. $^1$H NMR (400 MHz, DMSO-$d_6$) δ 8.69 (dd, J=2.4, 1.5 Hz, 1H), 7.71-7.55 (m, 5H), 7.15 (d, J=4.4 Hz, 1H), 6.96 (d, J=4.4 Hz, 1H), 6.34 (d, J=15.7 Hz, 1H), 3.76 (s, 3H). $^{13}$C NMR (100 MHz, DMSO-$d_6$) δ 182.4, 167.8, 143.2, 133.9, 133.8, 133.4, 131.2, 130.2, 127.5, 127.1, 120.1, 116.7, 113.4, 112.6, 30.6.

General Procedure for the Synthesis of 3-[4-(3-Aryl-3-oxopropen-1-yl)-1-methyl-1H-pyrrol-2-yl]-N-hydroxy-2-propenamides MJK001-003

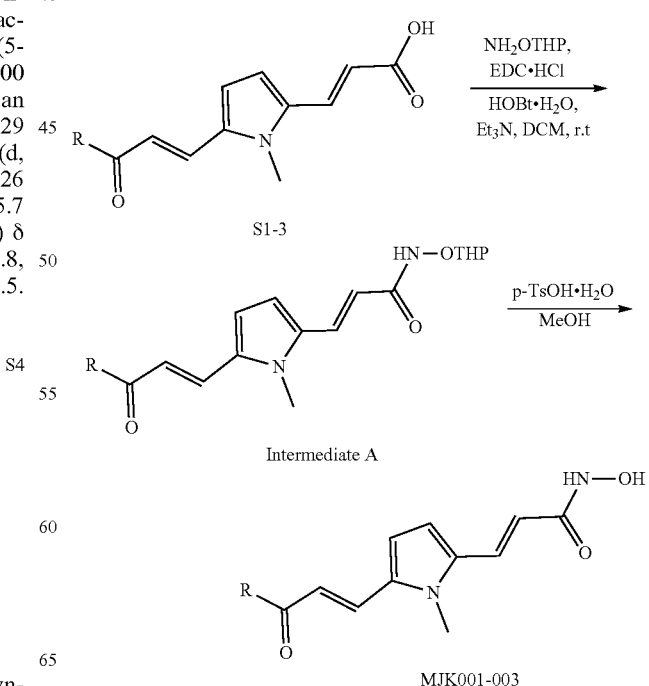

MJK001-003 were synthesized according to the method of Pfeffer and coworkers[2] using the following procedure.

(E)-3-(5-((E)-3-(3-Fluorophenyl)-3-oxoprop-1-en-1-yl)-1-methyl-1H-pyrrol-2-yl)-N-hydro-xyacrylamide, MJK001

N-ethyl-N'-(3-dimethylaminopropyl)carbodiimide hydrochloride (EDC·HCl, 2.89 g, 15.08 mmol), O-(tetra-hydro-2H-pyran-2-yl)hydroxylamine[3] ($NH_2OTHP$, 883 mg, 7.54 mmol), 1-hydroxybenzotriazole hydrate ($HOBt·H_2O$, 1.15 g, 7.54 mmol) and triethylamine ($Et_3N$, 3.68 ml, 26.39 mmol) was added to a stirring solution of (E)-3-(5-((E)-3-(3-fluorophenyl)-3-oxoprop-1-en-1-yl)-1-methyl-1H-pyrrol-2-yl)acrylic acid S1 (1.13 g, 3.77 mmol) in DCM (200.0 ml). After the reaction mixture was stirred at 22° C. for 16 h, it was washed with brine, dried over anhydrous $Na_2SO_4$, and filtered. The filtrate was condensed under reduced pressure and the residue was purified by silica gel flash column chromatography to provide compound Intermediate A (706 mg, 1.77 mmol, 47%, $R_f$=0.18 (2% in methanol in 1:1 EtOAc/petroleum spirits)) as a yellow oil. P-toluenesulfonic acid monohydrate (p-TsOH·$H_2O$, 101 mg, 0.531 mmol) was added to a stirring solution of Intermediate A (706 mg, 1.77 mmol) in MeOH (20.0 ml). After the starting material was consumed as indicated by TLC, an orange precipitate was isolated by gravity filtration and further purified by recrystallization from DMSO/$H_2O$ to afford the desired compound MJK001 (300 mg, 0.95 mmol, 54%) as an orange solid;

MJK001

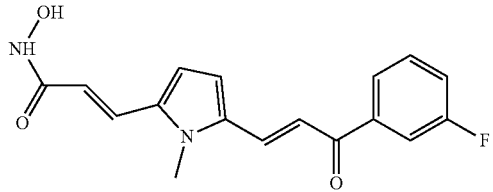

$^1$H NMR (400 MHz, DMSO-$d_6$) δ 10.71 (br s, 1H), 9.01 (br s, 1H), 7.97 (d, J=7.8 Hz, 1H), 7.90 (br d, J=9.8 Hz, 1H), 7.78 (d, J=14.9 Hz, 1H), 7.69-7.58 (m, 2H), 7.51-7.43 (m, 2H), 7.24 (d, J=4.2 Hz, 1H), 6.72 (d, J=3.9 Hz, 1H), 6.33 (d, J=15.6 Hz, 1H), 3.77 (s, 3H). $^{13}$C NMR (100 MHz, DMSO-$d_6$) δ 186.8 (d, $^4J_{C,F}$=2.3 Hz), 163.1, 162.4 (d, $^1J_{C,F}$=242.8 Hz), 140.4 (d, $^3J_{C,F}$=6.2 Hz), 135.1, 133.0, 131.9, 130.8 (d, $^3J_{C,F}$=7.7 Hz), 125.9, 124.3 (d, $^4J_{C,F}$=3.1 Hz), 119.6 (d, $^2J_{C,F}$=21.4 Hz), 118.1, 117.3, 114.7 (d, 2J$_{C,F}$=22.2 Hz), 114.2, 111.0, 30.6.

MJK002

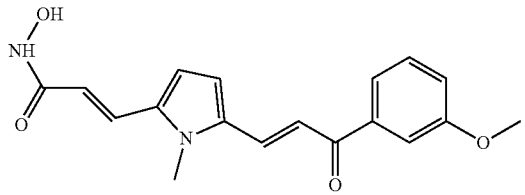

(E)-N-hydroxy-3-(5-((E)-3-(3-methoxyphenyl)-3-oxoprop-1-en-1-yl)-1-methyl-1H-pyrrol-2-yl)acrylamide, MJK002

This compound was synthesized according to the synthetic procedure for the preparation of MJK001 from (E)-3-(5-((E)-3-(3-methoxyphenyl)-3-oxoprop-1-en-1-yl)-1-methyl-1H-pyrrol-2-yl)acrylic acid S2 (209 mg, 0.67 mmol) in 52% overall yield (114 mg, 0.35 mmol) as an orange solid. $^1$H NMR (400 MHz, DMSO-$d_6$) δ 10.71 (br s, 1H), 9.02 (br s, 1H), 7.77-7.70 (m, 2H), 7.64 (d, J=15.2 Hz, 1H), 7.57 (br s, 1H), 7.49-7.49 (m, 2H), 7.22-7.19 (m, 2H), 6.71 (d, J=3.9 Hz, 1H), 6.33 (d, J=15.6 Hz, 1H), 3.84 (s, 3H), 3.76 (s, 3H). $^{13}$C NMR (100 MHz, DMSO-$d_6$) δ 187.9, 163.1, 159.5, 139.5, 134.9, 133.0, 131.4, 129.8, 125.9, 120.7, 118.7, 117.9, 117.8, 113.8, 112.8, 111.0, 55.3, 30.6.

MJK003

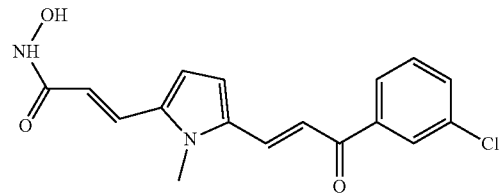

(E)-3-(5-((E)-3-(3-chlorophenyl)-3-oxoprop-1-en-1-yl)-1-methyl-1H-pyrrol-2-yl)-N-hydrox-yacrylamide, MJK003

This compound was synthesized according to the synthetic procedure for the preparation of MJK001 from (E)-3-(5-((E)-3-(3-chlorophenyl)-3-oxoprop-1-en-1-yl)-1-methyl-1H-pyrrol-2-yl)acrylic acid S3 (180 mg, 0.60 mmol) in 30% overall yield (60.0 mg, 0.18 mmol) as an orange solid. $^1$H NMR (400 MHz, DMSO-$d_6$) δ 10.73 (s, 1H), 9.04 (br s, 1H), 8.11 (s, 1H), 8.06 (d, J=7.6 Hz, 1H), 7.78 (d, J=14.9 Hz, 1H), 7.70-7.65 (m, 2H), 7.57 (t, J=7.8 Hz, 1H), 7.46 (d, J=15.6 Hz, 1H), 7.25 (d, J=4.2 Hz, 1H), 6.72 (d, J=3.4 Hz, 1H), 6.34 (d, J=15.4 Hz, 1H), 3.76 (s, 3H). $^{13}$C NMR (100 MHz, DMSO-$d_6$) δ 186.8, 163.0, 139.9, 135.2, 133.8, 133.0, 132.4, 132.0, 130.7, 127.8, 126.8, 125.9, 118.1, 117.2, 114.3, 111.0, 30.6.

Procedure for the Synthesis of (E)-N-hydroxy-3-(1-methyl-5-((E)-3-oxo-3-(thiophen-2-yl)prop-1-en-1-yl)-1H-pyrrol-2-yl)acrylamide, MJK004

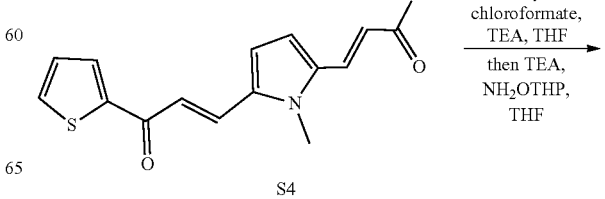

S4

Procedure for the Synthesis of (E)-N-hydroxy-3-(1-methyl-5-((E)-3-oxo-3-(thiophen-3-yl)prop-1-en-1-yl)-1H-pyrrol-2-yl)acrylamide hydrochloride, MJK005

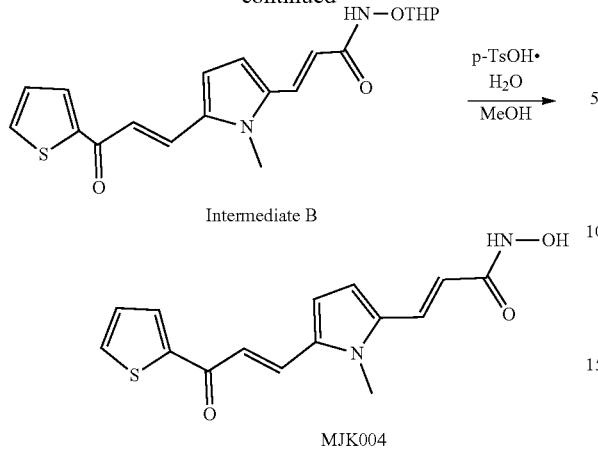

Intermediate B

MJK004

Ethyl chloroformate (0.119 ml, 1.25 mmol) was added to a solution of (E)-3-(1-methyl-5-((E)-3-oxo-3-(thiophen-2-yl)prop-1-en-1-yl)-1H-pyrrol-2-yl)acrylic acid S4 (300 mg, 1.04 mmol) and Et$_3$N (1.50 ml, 10.40 mmol) in dry THF (50.0 ml) and the resulting mixture was stirred at 0° C. for 10 min. The resultant was diluted with EtOAc and quenched with saturated NaHCO$_3$ (aq). The resultant was extracted twice with EtOAc, dried over anhydrous Na$_2$SO$_4$(s), and filtered. The filtrate was condensed under reduced pressure and the crude residue was dissolved in dry THF (25.0 ml). Et$_3$N (1.50 ml, 10.40 mmol) and a solution of NH$_2$OTHP (360 mg, 3.12 mmol) in dry THF (25.0 ml) was sequentially added to this cooled (0° C.) solution. The resulting mixture was stirred at 0° C. After completion of the reaction as indicated by TLC, the mixture was quenched with saturated NaHCO$_3$ (aq) and extracted twice with EtOAc. The combined organic layer was dried over anhydrous Na$_2$SO$_4$ and filtered. The filtrate was condensed under reduced pressure and the crude residue containing intermediate B was dissolved in methanol (10.0 ml). P-TsOH·H$_2$O (300 mg, 1.58 mmol) was added to this solution. After the starting material was consumed as indicated by TLC, the solvent was removed under reduced pressure and the residue was purified by recrystallization from DMSO/H$_2$O to afford the desired compound MJK004 (240 mg, 0.79 mmol, 76% overall yield) as a brown solid.

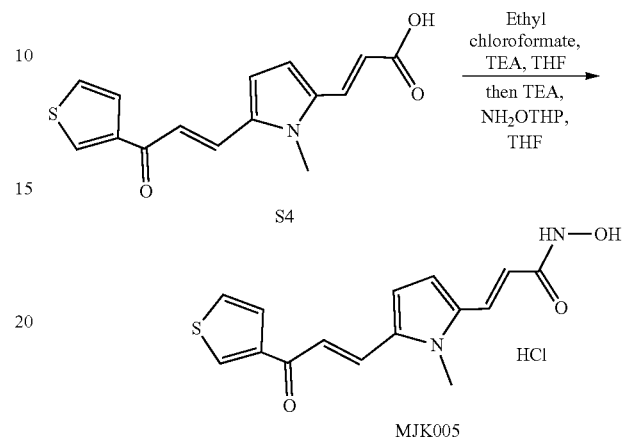

S4

MJK005

Ethyl chloroformate (0.159 ml, 1.67 mmol) was added to a solution of (E)-3-(1-methyl-5-((E)-3-oxo-3-(thiophen-3-yl)prop-1-en-1-yl)-1H-pyrrol-2-yl)acrylic acid S5 (400 mg, 1.39 mmol) and Et$_3$N (1.93 ml, 13.9 mmol) in dry THF (65.0 ml) and the resulting mixture was stirred at 0° C. for 10 min. The resultant mixture was diluted with EtOAc and quenched with saturated NaHCO$_3$ (aq). The mixture was extracted twice with EtOAc, dried over anhydrous Na$_2$SO$_4$, and filtered. The filtrate was condensed under reduced pressure and the crude residue was dissolved in dry THF (30.0 ml). Triethylamine (1.93 ml, 13.9 mmol) and a solution of NH$_2$OTHP (489 mg, 4.17 mmol) in dry THF (30.0 ml) was sequentially added to this cooled (0° C.) solution. The resulting mixture was stirred at 0° C. After the starting material was consumed as indicated by TLC, an orange precipitate was isolated by gravity filtration and washed by DCM and diethyl ether to afford the desired compound MJK005 (200 mg, 0.59 mmol, 42% overall yield) as an orange solid. In this case, the THP ether was removed during the final reaction to give the desired product.

MJK004

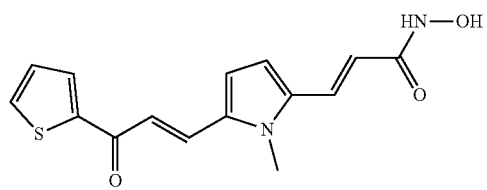

$^1$H NMR (400 MHz, DMSO-d$_6$) δ 10.72 (s, 1H), 9.03 (br s, 1H), 8.20 (d, J=3.2 Hz, 1H), 7.99 (d, J=4.9 Hz, 1H), 7.71 (d, J=14.9 Hz, 1H), 7.58 (d, J=15.2 Hz, 1H), 7.45 (d, J=15.4 Hz, 1H), 7.28 (dd, J=4.9, 3.9 Hz, 1H), 7.18 (d, J=4.2 Hz, 1H), 6.72 (d, J=3.9 Hz, 1H), 6.33 (d, J=15.4 Hz, 1H), 3.76 (s, 3H). $^{13}$C NMR (100 MHz, DMSO-d$_6$) δ 180.9, 163.1, 146.1, 134.9, 134.8, 132.8, 132.6, 130.5, 128.8, 125.9, 125.5, 117.9, 113.7, 111.0, 30.6.

MJK005

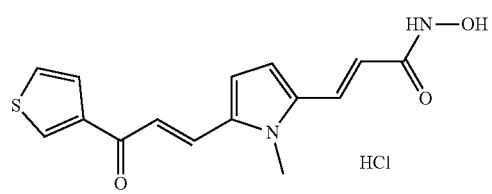

$^1$H NMR (400 MHz, DMSO-d$_6$) δ 9.32 (br s, 1H), 8.67 (s, 1H), 7.71-7.65 (m, 3H), 7.55 (d, J=14.9 Hz, 1H), 7.43 (d, J=15.6 Hz, 1H), 7.14 (d, J=4.2 Hz, 1H), 6.69 (d, J=4.2 Hz, 1H), 6.41 (d, J=14.9 Hz, 1H), 4.57 (br s, 1H), 3.75 (s, 3H). $^{13}$C NMR (100 MHz, DMSO-d$_6$) δ 182.4, 143.2, 134.7, 133.1, 132.9, 130.4, 127.4, 127.1, 125.8, 119.2, 113.4, 110.8, 30.6.

General Procedure for the Preparation of Methyl (E)-3-(1-methyl-5-((E)-3-oxo-3-aryl-prop-1-en-1-yl)-1H-pyrrol-2-yl)acrylates, S6-10

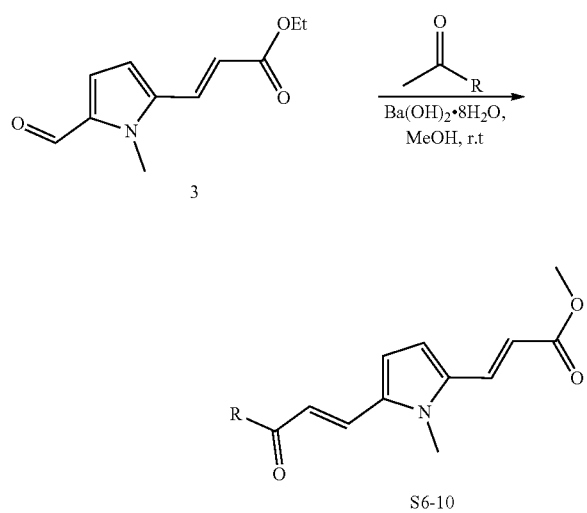

Methyl (E)-3-(1-methyl-5-((E)-3-oxo-3-(pyridin-3-yl)prop-1-en-1-yl)-1H-pyrrol-2-yl)-acry-late, S6

Barium hydroxide octahydrate (Ba(OH)$_2$·8H$_2$O, 4.57 g, 14.48 mmol) was added to a solution of 3-acetylpyridine (2.39 ml, 21.72 mmol) in methanol (70.0 ml) and the mixture was stirred at 22° C. for 15 min. Ethyl (E)-3-(5-formyl-1-methyl-1H-pyrrol-2-yl)-2-propenoate (3) (3.00 g, 14.48 mmol) was added to the resultant solution and the mixture was stirred at 22° C. After the ethyl (E)-3-(5-formyl-1-methyl-1H-pyrrol-2-yl)-2-propenoate (3) was consumed as indicated by TLC, the obtained precipitate was filtered and washed with water and ethanol to afford the desired product S6 (3.39 g, 3.77 mmol, 83%) as an orange-red solid.

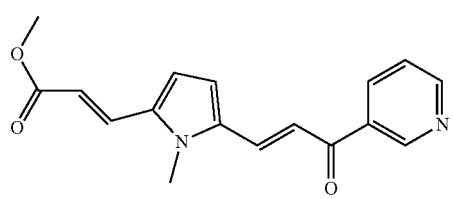

$^1$H NMR (400 MHz, CDCl$_3$) δ 9.22 (dd, J=2.2, 1.0 Hz, 1H), 8.78 (dd, J=4.6, 1.7 Hz, 1H), 8.28 (ddd, J=7.8, 2.2, 1.7 Hz, 1H), 7.86 (d, J=15.2 Hz, 1H), 7.63 (d, J=15.7 Hz, 1H), 7.44 (ddd, J=7.9, 4.8, 1.0 Hz, 1H), 7.34 (d, J=15.2 Hz, 1H), 6.92 (d, J=4.4 Hz, 1H), 6.75 (d, J=4.4 Hz, 1H), 6.30 (d, J=15.7 Hz, 1H), 3.80 (s, 3H), 3.78 (s, 3H). $^{13}$C NMR (100 MHz, CDCl$_3$) δ 188.0, 167.6, 153.2, 149.7, 135.8, 134.9, 134.0, 133.9, 132.0, 131.2, 123.8, 118.2, 116.6, 113.6, 112.8, 51.9, 31.0.

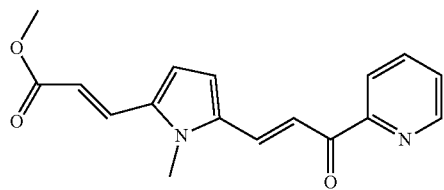

Methyl (E)-3-(1-methyl-5-((E)-3-oxo-3-(pyridin-2-yl)prop-1-en-1-yl)-1H-pyrrol-2-yl)acry-late, S7

This compound was synthesized according to the synthetic procedure for the preparation of S6 from ethyl (E)-3-(5-formyl-1-methyl-1H-pyrrol-2-yl)-2-propenoate (3) (2.00 g, 9.65 mmol) and 2-acetylpyridine (1.60 ml, 14.5 mmol) in 69% yield (2.00 g, 6.76 mmol) as an orange-red solid. $^1$H NMR (400 MHz, CDCl$_3$) δ 8.70 (ddd, J=4.6, 1.7, 1.0 Hz, 1H), 8.15 (dt, J=7.8, 1.1 Hz, 1H), 8.08 (d, J=15.4 Hz, 1H), 7.89-7.82 (m, 2H), 7.60 (d, J=15.6 Hz, 1H), 7.45 (ddd, J=7.5, 4.7, 1.2 Hz, 1H), 6.96 (d, J=4.4 Hz, 1H), 6.72 (d, J=4.4 Hz, 1H), 6.25 (d, J=15.4 Hz, 1H), 3.77 (s, 6H). $^{13}$C NMR (100 MHz, CDCl$_3$) δ 188.8, 167.7, 154.5, 148.9, 137.1, 134.8, 134.3, 131.4, 131.0, 126.8, 122.9, 118.6, 115.8, 113.8, 112.8, 57.8, 30.9.

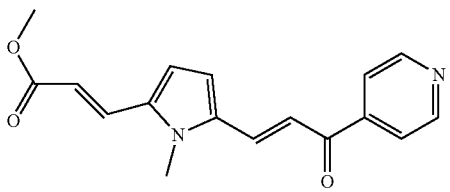

Methyl (E)-3-(1-methyl-5-((E)-3-oxo-3-(pyridin-4-yl)prop-1-en-1-yl)-1H-pyrrol-2-yl)acry-late, S8

This compound was synthesized according to the synthetic procedure for the preparation of S6 from ethyl (E)-3-(5-formyl-1-methyl-1H-pyrrol-2-yl)-2-propenoate (3) (1.50 g, 7.24 mmol) and 4-acetylpyridine (1.20 ml, 10.9 mmol) in 71% yield (1.52 g, 5.13 mmol) as an orange-red solid. $^1$H NMR (400 MHz, CDCl$_3$) δ 8.81-8.80 (m, 2H), 7.83 (d, J=15.2 Hz, 1H), 7.76-7.75 (m, 2H), 7.61 (d, J=15.6 Hz, 1H), 7.27 (d, J=14.9 Hz, 1H), 6.91 (d, J=4.4 Hz, 1H), 6.74 (d, J=4.4 Hz, 1H), 6.30 (d, J=15.7 Hz, 1H) 3.79 (s, 3H), 3.76 (s, 3H). $^{13}$C NMR (100 MHz, CDCl$_3$) δ 188.5, 167.5, 150.9, 144.8, 135.1, 133.9, 132.6, 131.1, 121.4, 117.8, 116.9, 113.8, 112.8, 51.9, 30.9.

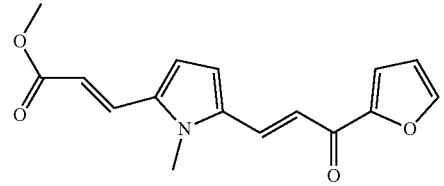

Methyl (E)-3-(5-((E)-3-(furan-2-yl)-3-oxoprop-1-en-1-yl)-1-methyl-1H-pyrrol-2-yl)acrylate, S9

This compound was synthesized according to the synthetic procedure for the preparation of S6 from ethyl (E)-3-(5-formyl-1-methyl-1H-pyrrol-2-yl)-2-propenoate (3) (1.00 g, 4.83 mmol) and 2-acetylfuran (0.727 ml, 7.25 mmol) in 77% yield (1.06 g, 3.72 mmol) as an orange solid. $^1$H NMR (400 MHz, CDCl$_3$) δ 7.73 (d, J=15.2 Hz, 1H), 7.56-7.51 (m, 2H), 7.21-7.17 (m, 2H), 6.79 (d, J=4.4 Hz, 1H), 6.65 (d, J=4.4 Hz, 1H), 6.50 (dd, J=3.4, 1.7 Hz, 1H), 6.19 (d, J=15.6 Hz, 1H), 3.71 (s, 3H), 3.68 (s, 3H). $^{13}$C NMR (100 MHz, CDCl$_3$) δ 177.5, 167.6, 154.0, 146.3, 134.3, 134.2, 131.3, 130.2, 118.8, 117.0, 115.9, 113.1, 112.63, 112.60, 51.8, 30.9.

Methyl (E)-3-(1-methyl-5-((E)-3-oxo-3-(pyrazin-2-yl)prop-1-en-1-yl)-1H-pyrrol-2-yl)acry-late, S10

This compound was synthesized according to the synthetic procedure for the preparation of S6 from ethyl (E)-3-(5-formyl-1-methyl-1H-pyrrol-2-yl)-2-propenoate (3) (2.00 g, 9.65 mmol) and acetylpyrazine (1.80 g, 14.5 mmol) in 79% yield (2.27 g, 7.64 mmol) as an orange-red solid. $^1$H NMR (400 MHz, CDCl$_3$) δ 9.34 (d, J=1.5 Hz, 1H), 8.74 (d, J=2.4 Hz, 1H), 8.66 (dd, J=2.4, 1.5 Hz, 1H), 7.96 (d, J=15.6 Hz, 1H), 7.91 (d, J=15.4 Hz, 1H), 7.61 (d, J=15.4 Hz, 1H), 6.98 (d, J=4.4 Hz, 1H), 6.74 (d, J=4.4 Hz, 1H), 6.29 (d, J=15.7 Hz, 1H), 3.792 (s, 3H), 3.785 (s, 3H). $^{13}$C NMR (100 MHz, CDCl$_3$) δ 187.8, 167.6, 148.8, 147.4, 144.9, 143.4, 135.0, 134.5, 131.7, 131.2, 117.5, 116.5, 113.3, 112.9, 51.9, 31.0.

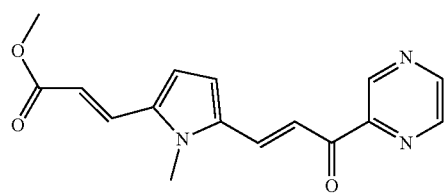

S10

Procedure for the Synthesis of (E)-N-Hydroxy-3-(1-methyl-5-((E)-3-oxo-3-(pyridin-3-yl)prop-1-en-1-yl)-1H-pyrrol-2-yl)acrylamide MJK006, and its Two Salt Forms, MJK008 and MJK009

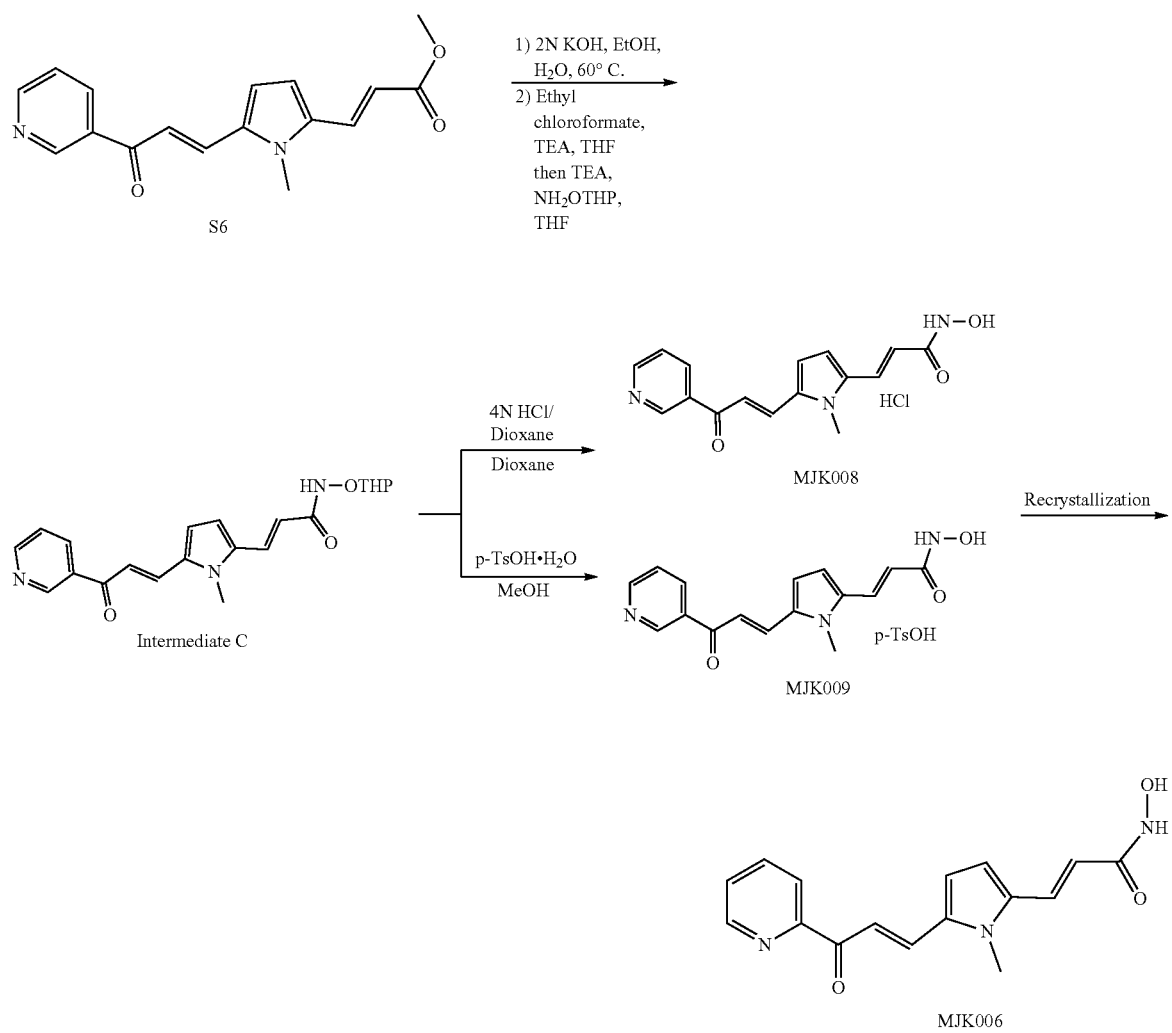

(E)-N-Hydroxy-3-(1-methyl-5-((E)-3-oxo-3-(pyridin-3-yl)prop-1-en-1-yl)-1H-pyrrol-2-yl)acrylamide hydrochloride, MJK008

2 N KOH (60.0 mmol, 30 ml) was added to a solution of methyl (E)-3-(1-methyl-5-((E)-3-oxo-3-(pyridin-3-yl)prop-1-en-1-yl)-1H-pyrrol-2-yl)-acrylate S6 (3.39 g, 3.77 mmol) in EtOH (35.0 ml) and water (35.0 ml) and the suspension was stirred at 60° C. until the orange solid completely dissolved. The reaction mixture was diluted with cold water and was made acidic with 2 N HCl. The obtained precipitate was collected by filtration to afford the crude resultant (3.20 g). The resulting orange solid (1.00 g) was dissolved in dry THF (170.0 ml). Et$_3$N (0.987 ml, 7.08 mmol) and ethyl chloroformate (0.405 ml, 4.25 mmol) were sequentially added to this solution and the resulting mixture was stirred at 0° C. for 10 min. The mixture was diluted with EtOAc and quenched with saturated NaHCO$_3$ (aq). The resulting mixture was extracted twice with EtOAc, dried over anhydrous Na$_2$SO$_4$, and filtered. The filtrate was condensed under reduced pressure and the crude resultant was dissolved in dry THF (85 ml). Triethylamine (0.987 ml, 7.08 mmol) and a solution of NH$_2$OTHP (1.20 g, 10.62 mmol) in dry THF (75 ml) was sequentially added to this solution and stirred at 0° C. After completion of the reaction as indicated by TLC, the mixture was quenched with saturated NaHCO$_3$ (aq) and extracted twice with EtOAc. The combined organic layer was dried over anhydrous Na$_2$SO$_4$ and filtered. The filtrate was condensed under reduced pressure and the crude residue containing intermediate C was dissolved in 1,4-dioxane (35.0 ml). A solution of 4 N HCl in 1,4-dioxane (3.0 ml) was added to this stirring solution and the reaction mixture was stirred at 22° C. for 1 h. The obtained precipitate was filtered and washed with DCM and diethyl ether to afford the desired product MJK008 (503 mg, 1.51 mmol, 39% overall yield) as an orange-red solid.

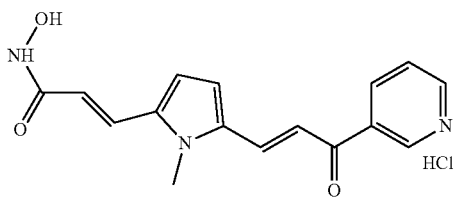

MJK008

$^1$H NMR (400 MHz, DMSO-d$_6$) δ 9.51 (s, 1H), 9.02 (d, J=5.1 Hz, 1H), 8.94 (d, J=7.6 Hz, 1H), 8.05 (dd, J=7.0, 6.0 Hz, 1H), 7.84 (d, J=14.7 Hz, 1H), 7.73 (d, J=14.9 Hz, 1H), 7.45 (d, J=15.2 Hz, 1H), 7.30 (d, J=3.7 Hz, 1H), 6.74 (d, J=3.2 Hz, 1H), 6.41 (d, J=15.4 Hz, 1H), 3.77 (s, 3H). HRMS(ESI+) Calcd for C$_{16}$H$_{16}$N$_3$O$_3$$^+$[M+H]$^+$ 298.1186, found 298.0950.

(E)-N-Hydroxy-3-(1-methyl-5-((E)-3-oxo-3-(pyridin-3-yl)prop-1-en-1-yl)-1H-pyrrol-2-yl)acrylamid p-toluenesulfonic acid salt, MJK009

2 N KOH (60.0 mmol, 30 ml) was added to a solution of methyl (E)-3-(1-methyl-5-((E)-3-oxo-3-(pyridin-3-yl)prop-1-en-1-yl)-1H-pyrrol-2-yl)-acrylate S6 (3.39 g, 3.77 mmol) in EtOH (35.0 ml) and water (35.0 ml) and the suspension was stirred at 60° C. until the orange solid completely dissolved. The reaction mixture was diluted with cold water and was made acidic with 2 N HCl. The obtained precipitate was collected by filtration to afford the crude product (3.20 g). The resulting orange solid (1.00 g) was dissolved in dry THF (170.0 ml). Et$_3$N (0.987 ml, 7.08 mmol) and ethyl chloroformate (0.405 ml, 4.25 mmol) were sequentially added and the resulting mixture was stirred at 0° C. for 10 min and then diluted with EtOAc and quenched with saturated NaHCO$_3$. The resulting mixture was extracted twice with EtOAc, dried over anhydrous Na$_2$SO$_4$, and filtered. The filtrate was condensed under reduced pressure and the crude residue was dissolved in dry THF (85.0 ml). Triethylamine (0.987 ml, 7.08 mmol) and a solution of NH$_2$OTHP (1.20 g, 10.62 mmol) in dry THF (85.0 ml) was sequentially added to this solution and the resulting mixture was stirred at 0° C. After completion of the reaction as indicated by TLC, the mixture was quenched with saturated NaHCO$_3$ (aq) and extracted twice with EtOAc. The combined organic layer was dried over anhydrous Na$_2$SO$_4$ and filtered. The filtrate was condensed under reduced pressure and the crude resultant containing intermediate C was dissolved in methanol (35.0 ml). To this stirring solution was added p-TsOH·H$_2$O (2.70 g, 14.16 mmol) and the reaction mixture was stirred at 22° C. for 1 h. The obtained precipitate was filtered and washed with DCM and diethyl ether to afford the desired product MJK009 (350 mg, 0.75 mmol, 20% overall yield) as an orange-red solid.

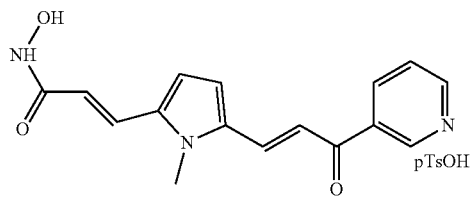

MJK009

$^1$H NMR (400 MHz, DMSO-d$_6$) δ 9.47 (d, J=1.7 Hz, 1H), 9.03 (dd, J=5.4, 1.2 Hz, 1H), 8.96 (dt, J=8.1, 1.5 Hz, 1H), 8.07 (dd, J=7.9, 5.5 Hz, 1H), 7.84 (d, J=14.9 Hz, 1H), 7.69 (d, J=14.9 Hz, 1H), 7.51 (d, J=8.1 Hz, 2H), 7.45 (d, J=15.4 Hz, 1H), 7.27 (d, J=4.4 Hz, 1H), 7.12 (d, J=7.8 Hz, 2H), 6.75 (d, J=4.2 Hz, 1H), 6.41 (d, J=15.4 Hz, 1H), 3.77 (s, 3H), 2.28 (s, 3H). $^{13}$C NMR (100 MHz, DMSO-d$_6$) δ 184.7, 162.9, 146.8, 145.2, 144.2, 142.4, 138.1, 136.2, 135.4, 133.2, 132.9, 128.2, 126.6, 125.7, 125.6, 118.9, 116.5, 115.2, 111.4, 30.7, 20.8. HRMS(ESI+) Calcd for C$_{16}$H$_{16}$N$_3$O$_3$$^+$ [M+H]$^+$ 298.1186, found 298.0954.

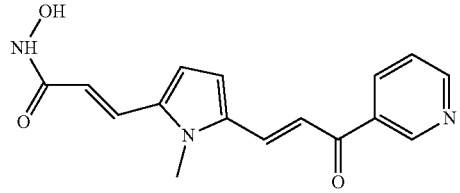

MJK006

(E)-N-hydroxy-3-(1-methyl-5-((E)-3-oxo-3-(pyridin-3-yl)prop-1-en-1-yl)-1H-pyrrol-2-yl)acrylamide, MJK006

This compound was synthesized through the recrystallization from DMSO/H$_2$O of MJK009 (350 mg, 0.75 mmol)

in 89% yield (188 mg, 0.67 mmol) as an orange solid. $^1$H NMR (400 MHz, DMSO-$d_6$) δ 10.74 (br s, 1H), 9.28 (s, 1H), 9.05 (br s, 1H), 8.79 (d, J=3.7 Hz, 1H), 8.41 (dt, J=7.9, 1.9 Hz, 1H), 7.79 (d, J=14.9 Hz, 1H), 7.67 (d, J=15.2 Hz, 1H), 7.58 (dd, J=7.9, 4.8 Hz, 1H), 7.45 (d, J=15.4 Hz, 1H), 7.24 (d, J=4.4 Hz, 1H), 6.72 (d, J=4.2 Hz, 1H), 6.34 (d, J=15.4 Hz, 1H), 3.77 (s, 3H). $^{13}$C NMR (100 MHz, DMSO-$d_6$) δ 187.2, 163.0, 152.9, 149.3, 135.7, 135.3, 133.3, 132.9, 131.9, 125.8, 123.9, 118.2, 117.4, 114.3, 111.1, 30.6. HRMS (ESI+) Calcd for $C_{16}H_{16}N_3O_3^+$ [M+H]$^+$ 298.1186, found 298.0951.

Procedure for the Synthesis of (E)-N-Hydroxy-3-(1-methyl-5-((E)-3-(1-methyl-1H-pyrrol-2-yl)-3-oxoprop-1-en-1-yl)-1H-pyrrol-2-yl)acrylamide, MJK007

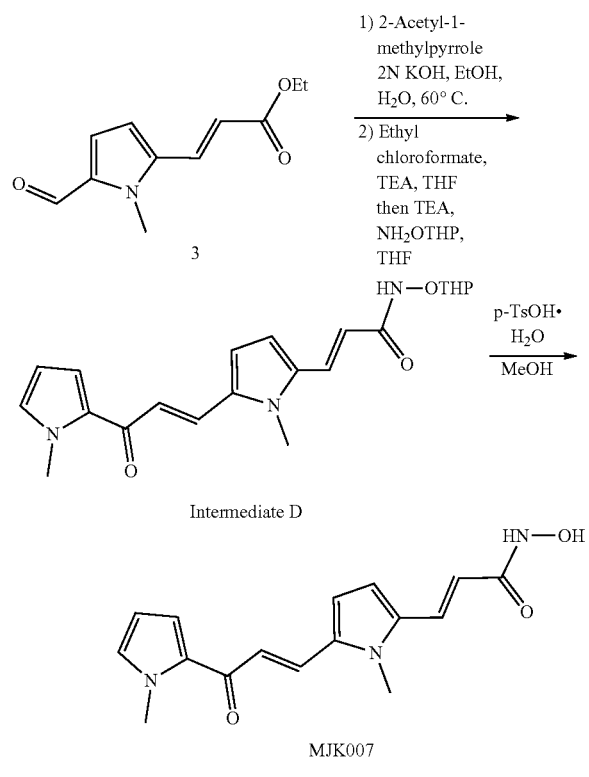

(E)-N-Hydroxy-3-(1-methyl-5-((E)-3-(1-methyl-1H-pyrrol-2-yl)-3-oxoprop-1-en-1-yl)-1H-pyrrol-2-yl)acrylamide, MJK007

2 N KOH (60 mmol, 40 ml) was added to a solution of 2-acetyl-1-methylpyrrole in EtOH (45.0 ml) and water (45.0 ml) and the mixture was stirred at 22° C. for 15 min. Ethyl (E)-3-(5-formyl-1-methyl-1H-pyrrol-2-yl)-2-propenoate (3) (3.00 g, 14.48 mmol) was added to the resultant solution and the mixture was stirred at 22° C. for 24 h. The suspension was then stirred at 60° C. until the yellow solid completely dissolved. The reaction mixture was diluted with cold water and was made acidic with 2 N HCl. The obtained precipitate was collected by filtration to afford the crude mixture (900 mg). This solid (900 mg) was dissolved in dry THF (150.0 ml). Et$_3$N (0.884 ml, 6.34 mmol) and ethyl chloroformate (0.362 ml, 3.80 mmol) were sequentially added to this solution and stirred at 0° C. for 10 min, then diluted with EtOAc and quenched with saturated NaHCO$_3$. The mixture was extracted twice with EtOAc, dried over anhydrous Na$_2$SO$_4$, and filtered. The filtrate was condensed under reduced pressure and the crude residue was dissolved in dry THF (75.0 ml). Triethylamine (0.884 ml, 6.34 mmol) and a solution of NH$_2$OTHP (1.11 g, 9.51 mmol) in dry THF (75.0 ml) was sequentially added to this cooled (0° C.) solution and the resulting mixture was stirred at 0° C. After completion of the reaction as indicated by TLC, the mixture was quenched with saturated NaHCO$_3$ (aq) and extracted twice with EtOAc. The combined organic layer was dried over anhydrous Na$_2$SO$_4$ and filtered. The filtrate was condensed under reduced pressure and the crude resultant containing intermediate D was dissolved in MeOH (35.0 ml). P-TsOH·H$_2$O (181 mg, 0.951 mmol) was added to this stirring solution. After the starting material was consumed as indicated by TLC, solvent was removed under reduced pressure and the residue was purified by recrystallization (DMSO/H$_2$O) to afford the desired compound MJK007 (217 mg, 0.72 mmol, 5% overall yield) as an orange solid.

$^1$H NMR (400 MHz, DMSO-$d_6$) δ 10.68 (br s, 1H), 9.02 (br s, 1H), 7.59 (d, J=15.2 Hz, 1H), 7.47-7.41 (m, 2H), 7.34 (dd, J=4.0, 1.6 Hz, 1H), 7.16 (t, J=1.7 Hz, 1H), 7.07 (d, J=4.2 Hz, 1H), 6.67 (d, J=3.7 Hz, 1H), 6.29 (d, J=15.4 Hz, 1H), 6.17 (dd, J=4.2, 2.4 Hz, 1H), 3.94 (s, 3H), 3.73 (s, 3H). $^{13}$C NMR (100 MHz, DMSO-$d_6$) δ 178.5, 133.8, 133.1, 132.1, 131.6, 128.0, 125.9, 120.7, 119.2, 116.9, 112.4, 110.6, 108.0, 37.2, 30.5 (one low-field carbon not observed).

General Procedure for the Synthesis of 3-[4-(3-Aryl-3-oxopropen-1-yl)-1-methyl-1H-pyrrol-2-yl]-N-hydroxy-2-propenamides, MJK010 and MJK011

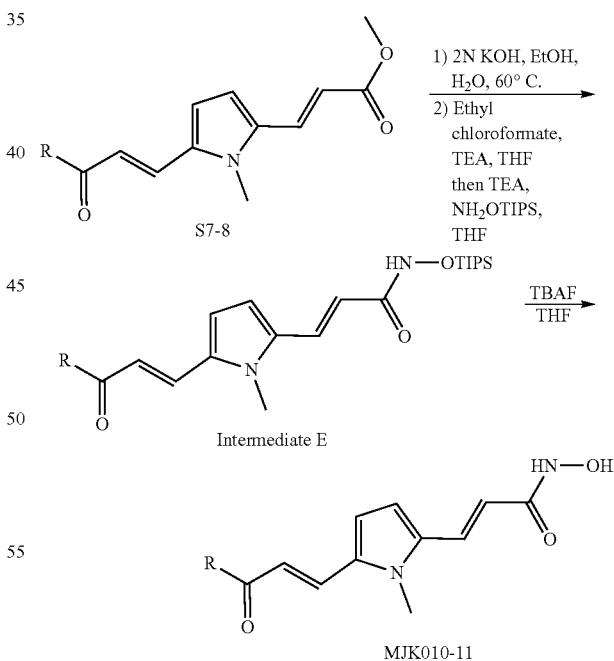

(E)-N-Hydroxy-3-(1-methyl-5-((E)-3-oxo-3-(pyridin-2-yl)prop-1-en-1-yl)-1H-pyrrol-2-yl)acrylamide, MJK010

2 N KOH (27.0 mmol, 13.5 ml) was added to a solution of methyl (E)-3-(1-methyl-5-((E)-3-oxo-3-(pyridin-2-yl)

prop-1-en-1-yl)-1H-pyrrol-2-yl)acrylate S7 (2.00 g, 6.76 mmol) in EtOH (20.0 ml) and water (20.0 ml) and the suspension was stirred at 60° C. until the orange solid completely dissolved. The reaction mixture was diluted with cold water and was made acidic with 2 N HCl. The obtained precipitate was collected by filtration to afford the crude residue as an orange solid. This orange solid was dissolved in dry THF (140.0 ml). Et₃N (1.90 ml, 13.52 mmol) and ethyl chloroformate (0.772 ml, 8.11 mmol) were sequentially added to this solution and the resulting mixture was stirred at 0° C. for 10 min. The mixture was diluted with EtOAc and quenched with saturated NaHCO₃ (aq). The mixture was extracted twice with EtOAc, dried over anhydrous Na₂SO₄, and filtered. The filtrate was condensed under reduced pressure and the crude residue was dissolved in dry THF (70.0 ml). Triethylamine (1.90 ml, 13.52 mmol) and a solution of O-(triiso-propylsilyl)hydroxylamine (NH₂OTIPS, 3.80 g, 20.3 mmol) in dry THF (70.0 ml) were sequentially added to this solution and the resulting mixture was stirred at 0° C. After completion of the reaction as indicated by TLC, the resultant was quenched with saturated NaHCO₃ (aq) and extracted twice with EtOAc. The combined organic layer was dried over anhydrous Na₂SO₄ and filtered. The filtrate was condensed under reduced pressure and the residue was purified with silica-gel flash column chromatography to provide compound Intermediate E (953 mg, 2.10 mmol, $R_f$=0.15 (EtOAc/Hexane=1:1)). Tetrabutylammonium fluoride (TBAF, 1.0 M solution in THF, 2.73 ml, 2.73 mmol) To a solution of Intermediate E in THE (20 ml) were added and the reaction mixture was stirred at 22° C. After the starting material was consumed as indicated by TLC, the solvent was removed under reduced pressure and the residue was purified by recrystallization from DMSO/H₂O to afford the desired compound MJK010 (100 mg, 0.34 mmol, 16% overall yield) as an orange solid.

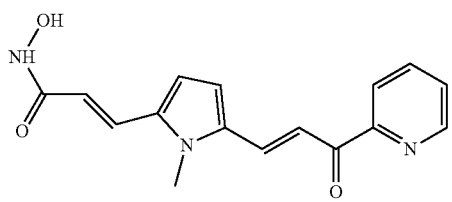

MJK010

¹H NMR (400 MHz, DMSO-d₆) δ 10.72 (br s, 1H), 9.02 (br s, 1H), 8.77 (d, J=4.2 Hz, 1H), 8.09-7.99 (m, 3H), 7.84 (d, J=15.6 Hz, 1H), 7.67-7.65 (m, 1H), 7.46 (d, J=15.6 Hz, 1H), 7.07 (d, J=4.2 Hz, 1H), 6.71 (d, J=3.9 Hz, 1H), 6.34 (d, J=15.2 Hz, 1H), 3.79 (s, 3H). ¹³C NMR (100 MHz, DMSO-d₆) δ 187.8, 162.9, 153.9, 149.1, 137.6, 135.3, 133.0, 131.4, 127.2, 125.7, 122.3, 118.3, 116.6, 113.7, 111.1, 30.7. HRMS (ESI+) Calcd for $C_{16}H_{16}N_3O_3^+$ [M+H]⁺ 298.1186, found 298.0888.

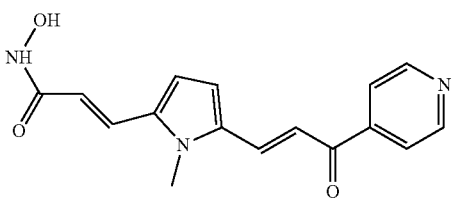

MJK011

(E)-N-hydroxy-3-(1-methyl-5-((E)-3-oxo-3-(pyridin-4-yl)prop-1-en-1-yl)-1H-pyrrol-2-yl)ac-rylamide, MJK011

This compound was synthesized according to the synthetic procedure for the preparation of MJK010 from methyl (E)-3-(1-methyl-5-((E)-3-oxo-3-(pyridin-4-yl)prop-1-en-1-yl)-1H-pyrrol-2-yl)acrylate S8 (1.52 g, 5.13 mmol) in 23% overall yield (0.089 mg, 0.30 mmol) as an orange solid. ¹H NMR (400 MHz, DMSO-d₆) δ 10.74 (br s, 1H), 9.04 (br s, 1H), 8.81 (d, J=5.4 Hz, 2H), 7.94 (d, J=5.6 Hz, 2H), 7.80 (d, J=14.9 Hz, 1H), 7.61 (d, J=15.2 Hz, 1H), 7.45 (d, J=15.4 Hz, 1H), 7.25 (d, J=4.2 Hz, 1H), 6.73 (d, J=3.7 Hz, 1H), 6.35 (d, J=15.6 Hz, 1H), 3.77 (s, 3H). ¹³C NMR (100 MHz, DMSO-d₆) δ 187.7, 162.8, 150.7, 144.2, 135.7, 132.84, 132.75, 125.7, 121.4, 118.5, 116.9, 114.6, 111.1, 30.6. HRMS(ESI+) Calcd for $C_{16}H_{16}N_3O_3^+$ [M+H]⁺ 298.1186, found 298.0886.

Procedure for the Synthesis of (E)-3-(5-((E)-3-(Furan-2-yl)-3-oxoprop-1-en-1-yl)-1-methyl-1H-pyrrol-2-yl)-N-hydroxyacrylamide MJK012

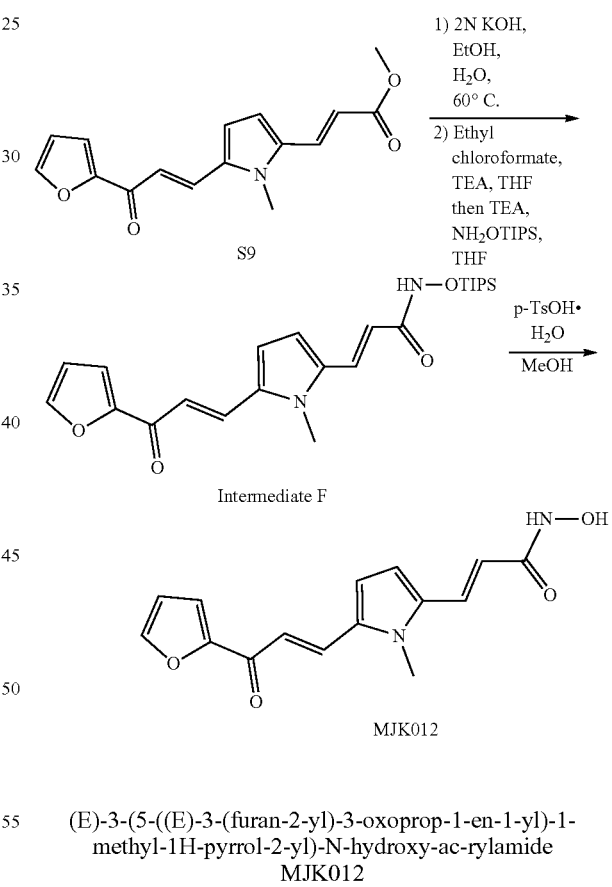

(E)-3-(5-((E)-3-(furan-2-yl)-3-oxoprop-1-en-1-yl)-1-methyl-1H-pyrrol-2-yl)-N-hydroxy-ac-rylamide MJK012

2 N KOH (14.9 mmol, 7.45 ml) was added to a solution of methyl (E)-3-(5-((E)-3-(furan-2-yl)-3-oxoprop-1-en-1-yl)-1-methyl-1H-pyrrol-2-yl)acrylate S9 (1.06 g, 3.72 mmol) in EtOH (10.0 ml) and water (10.0 ml) and the suspension was stirred at 60° C. until the orange solid completely dissolved. The reaction mixture was diluted with cold water and was made acidic with 2 N HCl. The obtained precipitate was collected by filtration to afford the crude residue as an orange solid. This orange solid was dissolved in dry THF (80.0 ml). Et₃N (1.00 ml, 7.44 mmol) and ethyl chloroformate (0.425 ml, 4.46 mmol) were sequentially added to this solution and the resulting mixture was stirred at 0° C. for 10 min. It was then diluted with EtOAc and quenched with saturated NaHCO₃ (aq). The mixture was extracted twice with EtOAc, dried over anhydrous Na₂SO₄, and filtered. The filtrate was condensed under reduced pressure and the crude resultant was dissolved in dry THF (40.0 ml). Triethylamine (1.00 ml, 7.44 mmol) and a solution of NH₂OTHP (2.00 g, 11.2 mmol) in dry THF (40.0 ml) was sequentially added to this stirring cooled (0° C.) solution and the resulting mixture was stirred at 0° C. After completion of the reaction as indicated by TLC, the reaction mixture was quenched with saturated NaHCO₃ (aq) and extracted twice with EtOAc. The combined organic layer was dried over anhydrous Na₂SO₄ and filtered. The filtrate was condensed under reduced pressure and the residue was purified by silica gel flash column chromatography to provide compound Intermediate F (650 mg, 1.75 mmol R$_f$=0.50 (DCM/methanol=20:1). P-TsOH·H₂O (100 mg, 0.53 mmol) was added to a stirring solution of Intermediate F (650 mg, 1.75 mmol) in MeOH (30 ml). After the starting material was consumed as indicated by TLC, the solvent was removed under reduced pressure and the residue was purified by recrystallization from DMSO/H₂O to afford the desired compound MJK012 (250 mg, 0.87 mmol, 23% overall yield) as an orange solid.

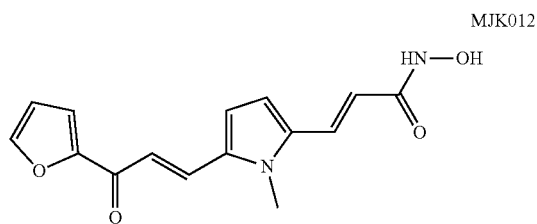 [SMILES: Cn1c(/C=C/C(=O)NO)ccc1/C=C/C(=O)c1ccco1]

MJK012

$^1$H NMR (400 MHz, DMSO-d₆) δ 10.72 (br s, 1H), 9.05 (br s, 1H), 8.02 (dd, J=1.6, 0.6 Hz, 1H), 7.71 (d, J=15.2 Hz, 1H), 7.66 (d, J=3.2 Hz, 1H), 7.47-7.40 (m, 2H), 7.12 (d, J=4.2 Hz, 1H), 6.75 (dd, J=3.7, 1.7 Hz, 1H), 6.70 (d, J=4.2 Hz, 1H), 6.33 (d, J=15.7 Hz, 1H), 3.75 (s, 3H). $^{13}$C NMR (100 MHz, DMSO-d₆) δ 176.3, 163.1, 153.3, 147.8, 134.8, 132.8, 130.1, 125.9, 118.2, 118.0, 117.8, 113.5, 112.6, 111.0, 30.6.

Procedure for the Synthesis of (E)-N-Hydroxy-3-(1-methyl-5-((E)-3-oxo-3-(pyrazin-2-yl)prop-1-en-1-yl)-1H-pyrrol-2-yl)acrylamide hydrochloride, MJK013

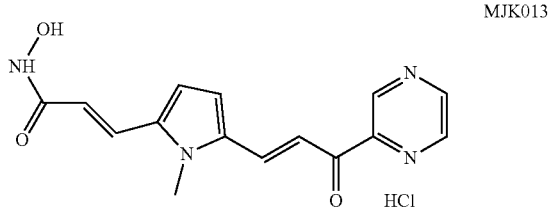 [SMILES: Cn1c(/C=C/C(=O)NO)ccc1/C=C/C(=O)c1cnccn1 ; Cl]

MJK013

(E)-N-Hydroxy-3-(1-methyl-5-((E)-3-oxo-3-(pyrazin-2-yl)prop-1-en-1-yl)-1H-pyrrol-2-yl)acrylamide hydrochloride, MJK013

This compound was synthesized according to the synthetic procedure for the preparation of MJK008 from methyl (E)-3-(1-methyl-5-((E)-3-oxo-3-(pyrazin-2-yl)prop-1-en-1-yl)-1H-pyrrol-2-yl)acrylate S10 (2.27 g, 7.64 mmol) in 7% overall yield (50 mg, 0.15 mmol) as an orange-red solid. $^1$H NMR (400 MHz, CDCl₃) δ 10.80 (br s, 1H), 9.08 (br s, 1H), 7.92 (d, J=5.6 Hz, 1H), 7.51-7.21 (m, 4H), 6.73 (s, 2H), 6.58 (d, J=3.7 Hz, 1H), 6.36 (d, J=15.4 Hz, 1H), 3.61 (s, 3H). $^{13}$C NMR (100 MHz, CDCl₃) δ 163.3, 145.3, 139.2, 132.5, 126.4, 124.5, 121.0, 119.8, 116.6, 116.2, 115.8, 111.7, 109.9, 105.2, 32.2.

Example 2: Methods for In Vitro and In Vivo Studies

Animals

Male C57BL/6J mice 8-10 weeks old were purchased from The Jackson Laboratory (Sacramento, CA, USA). Mice were housed 4 per cage, maintained on a 12:12 hour light-dark cycle and given access to food and water ad libitum. Following an acclimatization period of 3 to 5 days, trinitrobenzene sulfonic acid (TNBS, Millipore Sigma, St. Louis, MO, USA) colitis was induced by intracolonic (i.c.) injection of 0.05 ml TNBS solution (5 mg in 40% ethanol) via a polyethylene cannula (BD Intramedic PE-20 tubing, Thermo Fisher Scientific, Santa Clara, CA, USA) inserted 3.5 cm from the anal verge under isoflurane anesthesia (4% in O₂ induction, 2.5-3% maintenance). Control mice received an injection of 40% ethanol (0.05 ml, i.c.). To test the effectiveness of the HDAC analogs, mice received a daily injection (0.1 ml, i.c.) of a selective HDAC class II inhibitor analog (50 mg/kg MJK001-013) or vehicle (5% dimethyl sulfoxide, Millipore Sigma) beginning one day prior to TNBS colitis induction (day −1) for a period of 5 days. Separate groups of mice received HDAC inhibitors or vehicle administered by daily oral gavage (50 mg/kg, 0.25 ml, p.o.). All analogs tested were first dissolved in dimethyl sulfoxide (DMSO) with rapid vortexing and subsequent dilution to 5% in sterile phosphate buffered saline (PBS; Gibco, Thermo Fisher Scientific). Vehicle contained 5% DMSO in sterile PBS. Prior to use, all solids were stored in amber (light-blocking) storage vials at 4° C. On the first day of administration, stock solutions were prepared, aliquoted and stored at −20° C. for daily use. Upon thawing, each aliquot was vortexed prior to intracolonic injection (via a polyethylene cannula) or oral gavage (20 ga×38 mm, Instech, Thermo Fisher Scientific). Following all in vivo experiments, animals were euthanized on day 4 by CO₂ inhalation and cervical dislocation and the distal colons removed for further study.

Disease Severity Measurements

Disease severity was assessed by weight loss and measurement of colon length and determination of clinical and histological damage scores on day 4 of the protocol. Briefly, clinical scores were calculated on a scale of 0-3 for degree of weight loss, bleeding, stool consistency and presence of rectal prolapse. Sections of colon (5 μm) fixed in 10% formalin, paraffin-embedded and stained with hematoxylin and eosin (H&E) were used for histological scoring using an AxioImager. Z1 microscope equipped with AxioVision software version 4.6 (Zeiss, Jena, Germany). Scoring was performed by two independent investigators blinded to the treatment conditions and resulting scores averaged. Scores were assigned based on the degree of crypt damage (0-4), polymorphonuclear neutrophil (PMN) infiltrate (0-3), erosion (0-3), and edema (0-3).

Animal Models Statistical Analysis

Statistical analyses were performed using GraphPad Prism (Version 5.0a; GraphPad Software, La Jolla, CA, USA). Differences were determined by unpaired t-test, 1-way analysis of variance, or a 2-way analysis of variance with Tukey's post-test. A p value <0.05 was considered to be statistically significant. Data presented are means±SEM for n animals.

Fluorogenic HDAC Activity Assay

To measure the effects of MJK-001, -004, -006 and -008 on HDAC4 & 9 activity fluorogenic HDAC9 (#50069) and HDAC4 (#50064) assay kits (BPS Bioscience) were used. Briefly, these assays consist of two steps; in the first one the HDAC fluorometric substrate containing an acetylated lysine side chain is incubated with purified HDAC9. In the second step, the deacetylation sensitizes the substrate so subsequent treatment with the lysine developer produces a fluorophore that was measured by a fluorescence reader.

Cell Lines

Pancreatic cancer cell lines (MIA PaCa-2 and CAPAN-2) were purchased from ATCC. MIA PaCa-2 were grown in DMEM and CAPAN-2 in McCoy's 5A (Gibco). Colon cancer cell lines (SW480 and HT-29) were purchased from ATCC. SW480 were grown in Leibovitz's L-15 (ATCC) and HT-29 in McCoy's 5A (Gibco). Lung cancer cell lines (NCI 460 and NCI 1975) were purchased from ATCC and grown in RPMI 1640 (Gibco). PC-3 prostate cancer cell line was purchased from ATCC and grown in F-12K (ATCC). Bladder cancer cell line 5637 was purchased from ATCC and RT-112 was purchased from Sigma-Aldrich and was grown in RPMI 1640 (Gibco). Bladder cancer cell lines, UMUC-9, UMUC-15 and UMUC-7 were purchased from MD Anderson and were grown in EMEM (ATCC). Bladder cancer cell line J82 was purchased from ATCC and was grown in EMEM (ATCC). SW1710 and EJ28 bladder cancer cell lines were purchased from DSMZ and were grown in DMEM (ATCC) and RPMI-1640 (Gibco), respectively. Bladder cancer cell line T24 was purchased from ATCC and grown in McCoy's 5A (Gibco). Bladder cancer cell line BC-3C was purchased from DSMZ and was grown in McCoy's 5A (Gibco). All media were supplemented with 10% FBS (Gemini Bioproducts) and 1% Antibiotic-Antimycotic (Gibco). In the case of MIA PaCa-2, medium was also supplemented with 2.5% horse serum (Gibco). NCM356 colon epithelial cell lines were growth in M3:10 (INCELL, San Antonio, Tex.). A CMV-driven-HDAC9 vector was used to overexpress HDAC9 levels in NCM356 cells. IL1B and TNFA mRNA levels were measured by qPCR analysis as described previously (Fang K et al. Am J Pathol, 188(3): 586-99, 2018).

Cell Viability Assay $1.8 \times 10^3$ cells/well were plated in quadruplicates in 96-well plate and treated with exogenously added MJK analogues 6 hours after plating. For the experiments performed to calculate the IC50s of HDAC9 analogues, a secondary treatment of exogenously added MJK analogues was performed 2 days later. Cell growth was assessed 1, 3, 5 or 7 days after plating using the CellTiter Glo Luminescence Cell Viability Assay (Promega) according to manufacturer's protocol. For the experiments where the effect of combinatorial treatment of MJK-004 analogues with chemotherapy was assessed, treatment of cells with gemcitabine (10 nM) or 5-fluouracil (2000 nM) was performed one day after MJK-004 treatment and the cells were further treated with exogenously added MJK analogues 2 days later. Cell growth was assessed 3, 4, 5 or 6 days after plating using the CellTiter Glo Luminescence Cell Viability Assay (Promega) according to manufacturer's protocol. Data are expressed as mean fluorescence (arbitrary units)±S.D.

Cell Treatments for IC50 Calculation

Cell Viability Assays were employed to determine the concentration of MJK analogues where the response is reduced by half. For each treatment of cancer cells, 1, 2, 5, 10 and 20 µM of MJK analogues were applied. GraphPad Prism 7 software was used to fit dose response curves. Relative Luciferase Activity Units were plotted against the log values of the doses used and the nonlinear regression model was used for data analysis.

Anchorage-Independent Cell Growth Assay

Quadruplicate samples of $1 \times 10^6$ bladder cancer cells, that were previously untreated or treated with the MJK-004 at the concentration corresponding to the 1×IC50 or 2×IC50 for each cell line (as assessed at the third day after cells' plating and treatment) for 3 days, were assayed in 96-well plates for colony formation using the CytoSelect Cell Transformation kit (Cell Biolabs, Inc) according to manufacturer's protocol. Seven days later, live cells were detected using a colorimetric format. The MTT dye was added directly to the cultured cells followed by a detergent solution. Quantitation was performed using a standard microplate reader at 540-570 nm. Data were expressed as the mean±S.D.

RNA-Sequencing & Gene Network Analysis

RNA was extracted from bladder cancer cells that were previously treated with the MJK-004 at the concentration corresponding to the 1×IC50 for each cell line (as assessed at the third day after cells' plating and treatment) for 3 days, using TRIZOL (Life Technologies) and subsequently the RNAeasy Plus kit (Qiagen). Analytical quality control of the samples was performed using the Agilent 2100 Bioanalyzer System.

RNA-Sequencing methodology is divided in the 3 following parts and has been conducted at the UCLA Clinical Microarray Core. Part 1: method summary: Libraries for RNA-Seq were prepared with KAPA Stranded RNA-Seq Kit. The workflow consists of mRNA enrichment, cDNA generation, and end repair to generate blunt ends, A-tailing, adaptor ligation and PCR amplification. Different adaptors were used for multiplexing samples in one lane. Sequencing was performed on the Illumina HiSeq 3000 for a single read 50 run. Data quality check was performed with the Illumina SAV. Demultiplexing was performed with the Illumina Bcl2fastq2 v 2.17 program.

The reads were first mapped to the latest UCSC transcript set using Bowtie2 version 2.1.0 [1] and the gene expression level was estimated using RSEM v1.2.15 [2]. TMM (trimmed mean of M-values) was used to normalize the gene expression. Differentially expressed genes were identified using the edgeR program [3]. Genes showing altered expression with p<0.05 and more than 1.5-fold changes were considered differentially expressed.

Part 2: Result: Samples_PCA.tiff=>Principal Component Analysis plot on the TMM normalized gene expression.

rsem_count.txt=>Expected read count produced by RSEM for each gene in each sample. The differential expression analysis is based on this file.

TMM_normalized_reads_count_per_million.txt=> Normalized gene expression data by TMM method XXX_vs_YYY folders=>Contains the corresponding comparisons of group XXX against YYY. In them, you will find the following:

XXX_vs_YYY_all.txt=>Differential expression analysis results (fold-change, pvalue, FDR, etc. . . . ) based on the gene normalized read counts from the comparison XXX_vs_YYY.

XXX_vs_YYY_atfc1.5p0.05_ZZZ_genes.txt=> Differentially expressed genes list, as defined by having a fold-change of at least 1.5 and p-value less than 0.05.

XXX_vs_YYY_atfc1.5p0.05_ZZZ_genes_heatmap. tiff=>Heatmap of the previous file.

IPA folder=>IPA gene network data analysis

RSEM output folder=>Contain the raw output files of the RSEM analysis to get read counts for each gene/transcript (read count, TPM, FPKM, etc. . . . ).

Part 3: Reference: Fast gapped-read alignment with Bowtie 2. Langmead B, Salzberg SL. Nat Methods. (2012), RSEM: accurate transcript quantification from RNA-Seq data with or without a reference genome. Li B et al. BMC Bioinformatics. (2011), EdgeR: a Bioconductor package for differential expression analysis of digital gene expression data. Robinson MD1, McCarthy D J, Smyth G K. Bioinformatics. (2010).

Example 3: Results from In Vitro and In Vivo Studies

Epigenetic alterations have been involved in the pathogenesis of cancer and different auto-immune diseases, including Crohn's Disease, Ulcerative Colitis, Lupus and Rheumatoid Arthritis. Histone deacetylases (HDACs) are enzymes that catalyze the removal of acetyl functional groups from the lysine residues of both histone and non-histone proteins. HDAC enzymes are divided into 4 different classes: Class I (HDAC 1,2,3,8), Class II (HDAC4,5,6,7,9, 10), Class III (SIRT1-7) and Class IV (HDAC11). Specifically, HDACs 4, 5, 7, & 9 consist the Class IIA. Although there are HDAC inhibitors targeting all (pan-HDAC) HDAC isoforms or specific classes, there is an unmet need to develop HDAC inhibitors that have high specificity for unique HDAC isoforms. This is based on the fact that different HDAC isoforms could have opposing functions in the pathogenesis of the same disease.

Novel chemical HDAC inhibitors were developed aiming to target specific isoforms of the HDAC Class IIA members. Overall, as shown above, compounds have been synthesized, named MJK-001, -002, -003, -004, -005, -006, -007, -008, -009, -010, -011, -012 & -013. The effect of selective HDAC class IIA isoform inhibition during development of colitis in mice in vivo during TNBS administration was assessed. This mouse model is known to recapitulate many features of human Crohn's Disease. Mice received either an intracolonic (i.c.) injection or oral delivery (p.o.) of the MJK compounds once daily for a period of 5 days and health status, weight loss, and disease activity were monitored. Mice (male C57BL/6J, 8-10 wks old) are weighed and monitored daily. On the final day, blood, feces, and colonic samples for RNA, protein and histology are collected for downstream analysis.

Clinical Score Assessment
Weight loss:
0, no weight loss;
1, <5% weight loss;
2, <10% weight loss;
3, <15% weight loss.
Blood:
0, no bleeding
1, some bleeding
2, visible blood in the stool
3, gross bleeding
Stool consistency:
0, normal
1, soft
2, very soft
3, diarrhea
Rectal Prolapse:
0, none
1, signs of prolapse
2, clear prolapse
3, extensive prolapse
Total possible score=12

As expected, mice with TNBS colitis lost approximately 20% of their body weight compared to control animals over the duration of the 5-day protocol, demonstrating effective colitis induction in all mice tested. TNBS colitis also induced colon shortening and increased clinical and histological scores as compared to controls, consistent features of multiple animal models that indicate the severity of the disease. MJK compounds that exhibited significant differences from controls were subjected to further analysis, including histological scoring of H&E-stained sections and additional in vivo testing of analogs via oral gavage.

Figure 1B:
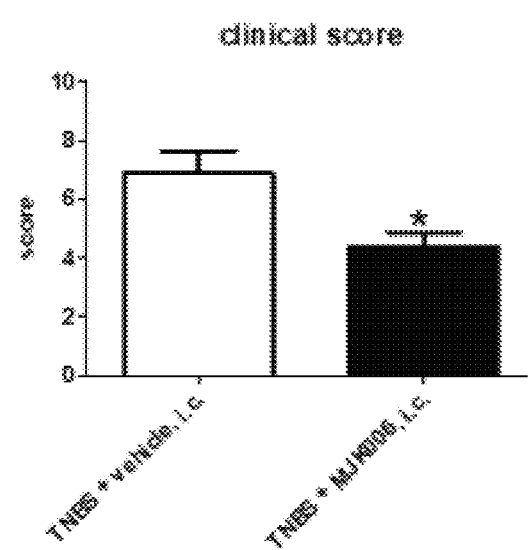
Figure 1C:
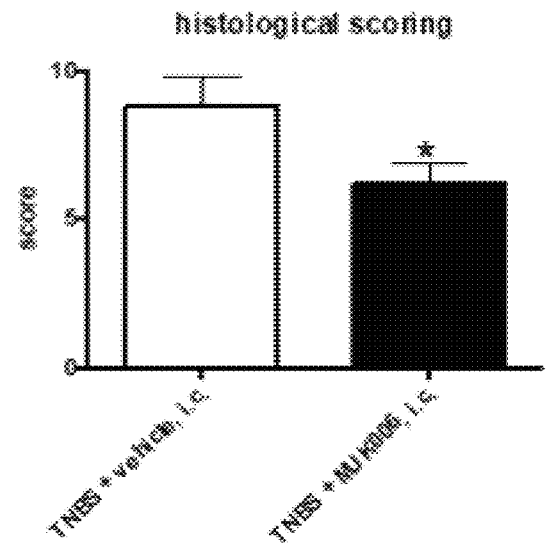
Figure 1D:
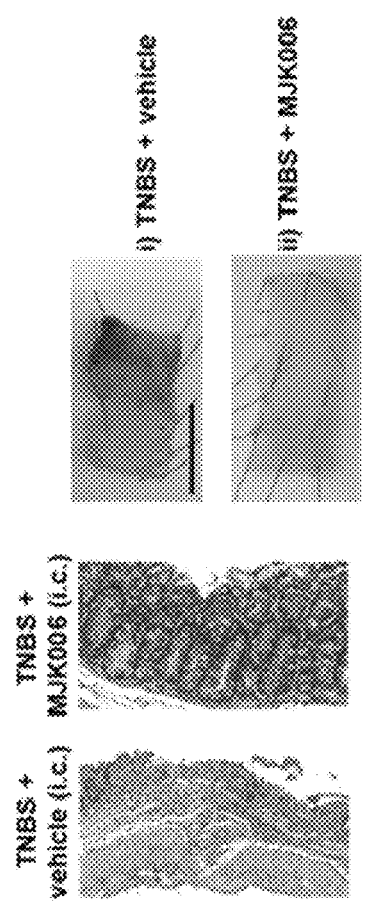
Figure 2A:
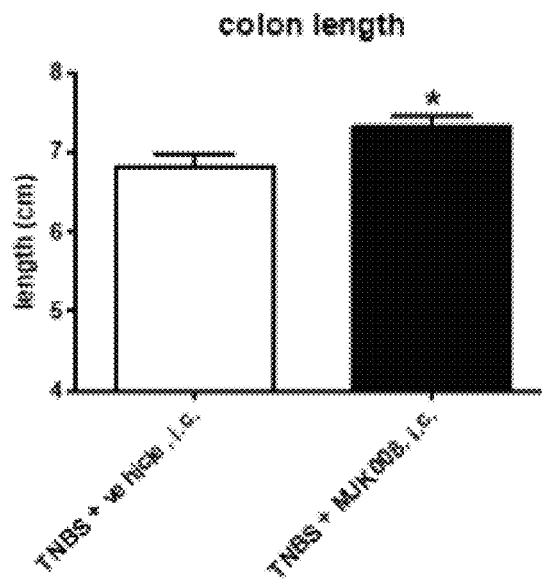
FIGS. 2A-2D show MJK-008 had significant effect in preserving colon length and decreasing the clinical and histological score in comparison to untreated mice. Histological sections show that TNBS induces crypt damage, which was significantly restored after MJK-008 treatment.
Figure 2B:
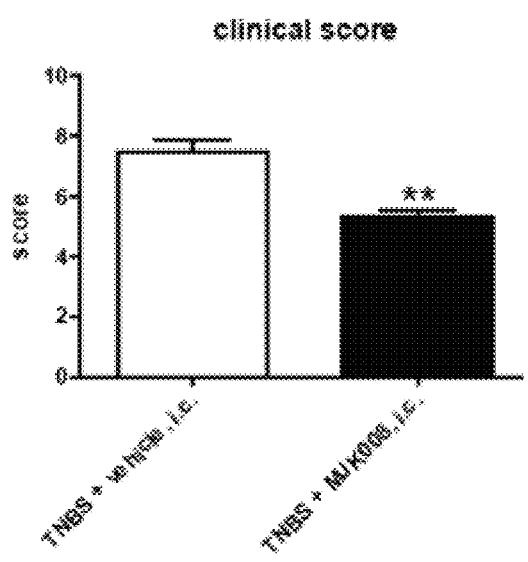
Figure 2C:
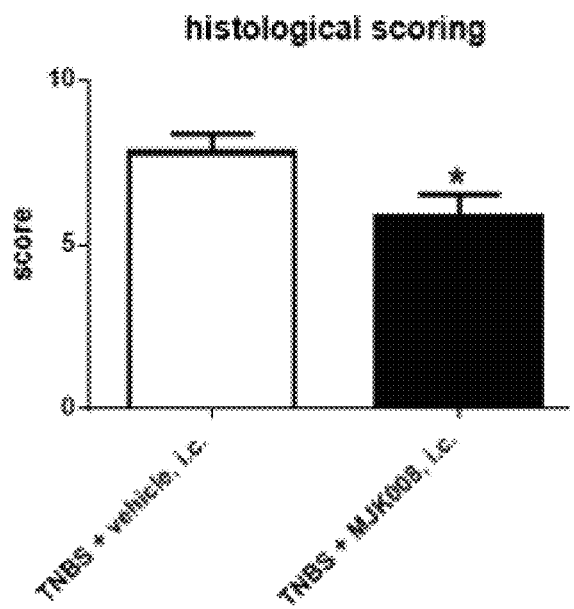
Figure 2D:
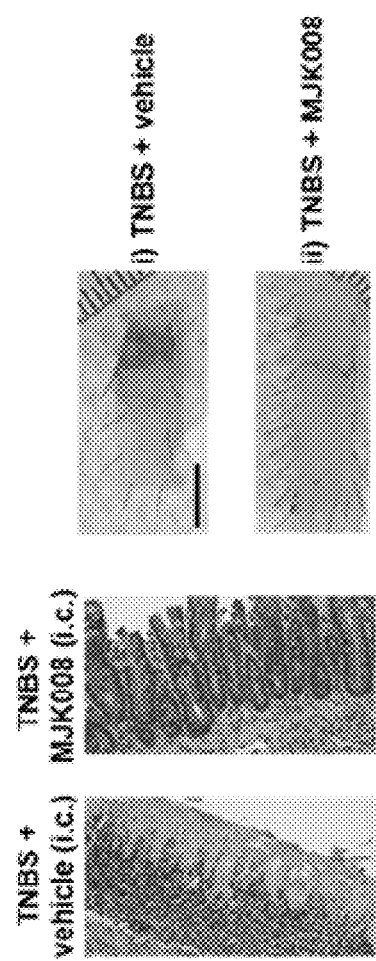
Figure 3A:
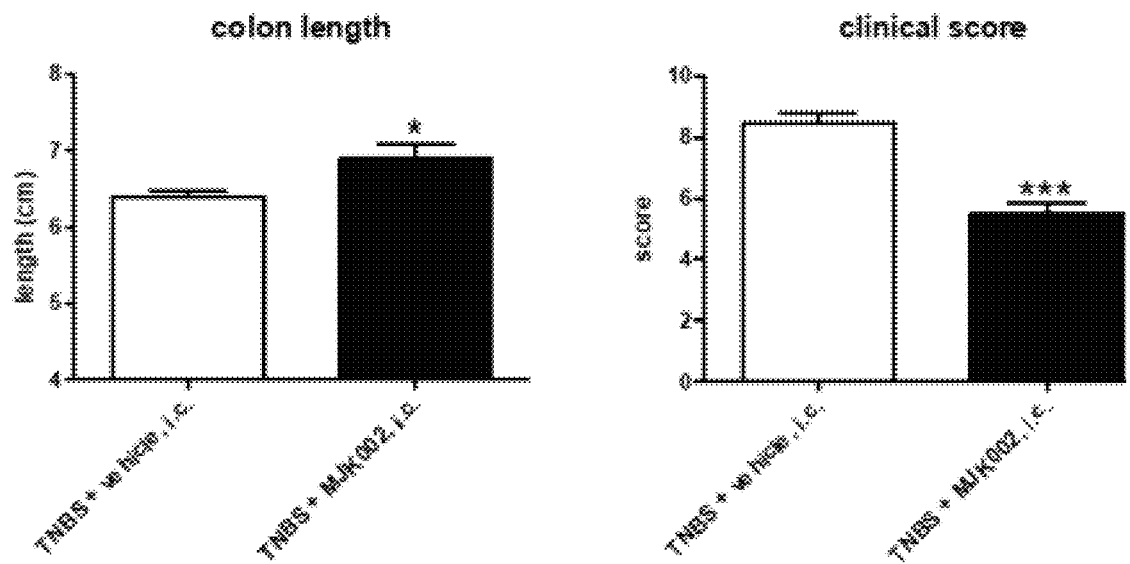
FIGS. 3A-3C show mice treated with MJK-001, MJK-002 and MJK-003 showed statistical significance in the reduction of the clinical score and increase of colon length.
Figure 3B:
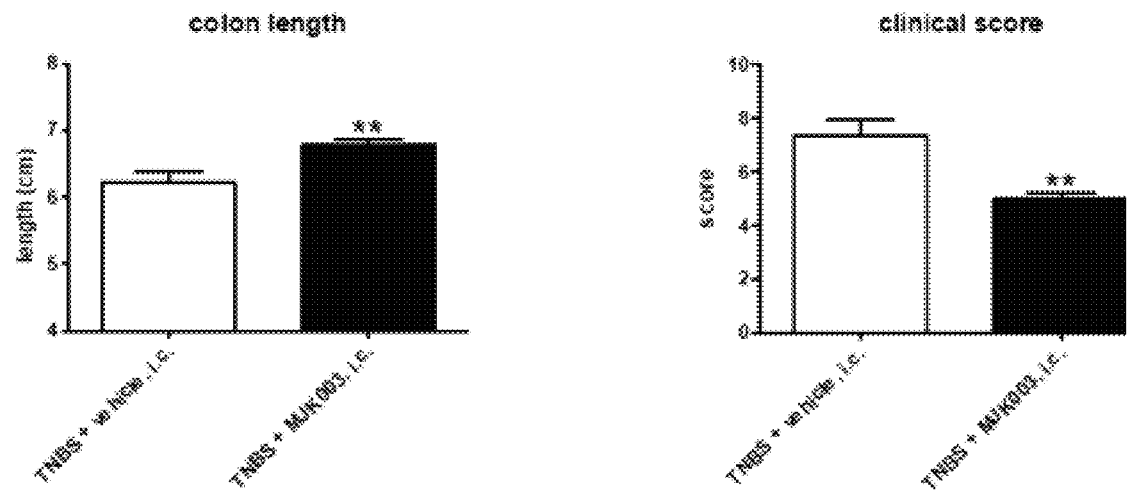
Figure 3C:
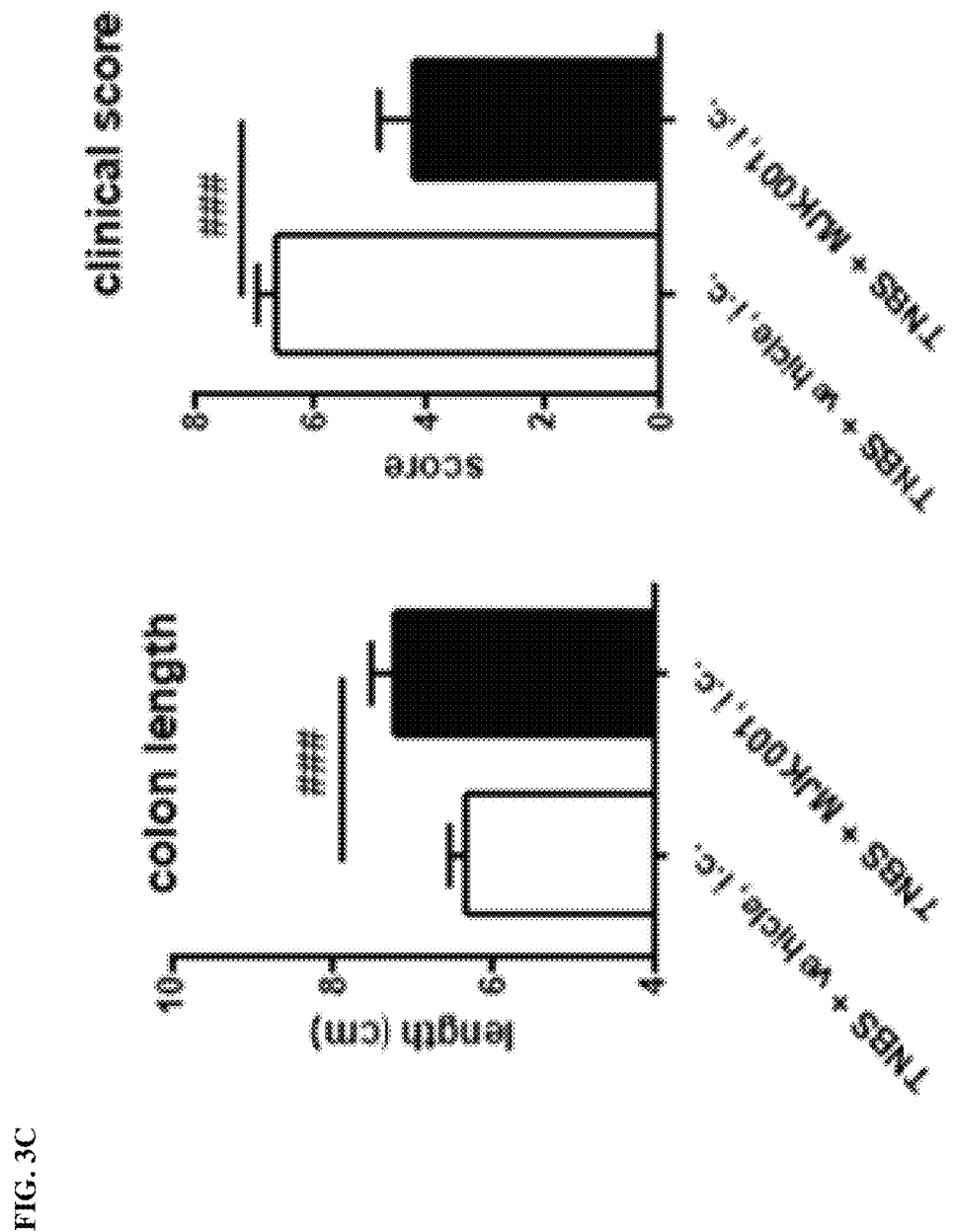
Figure 4A:
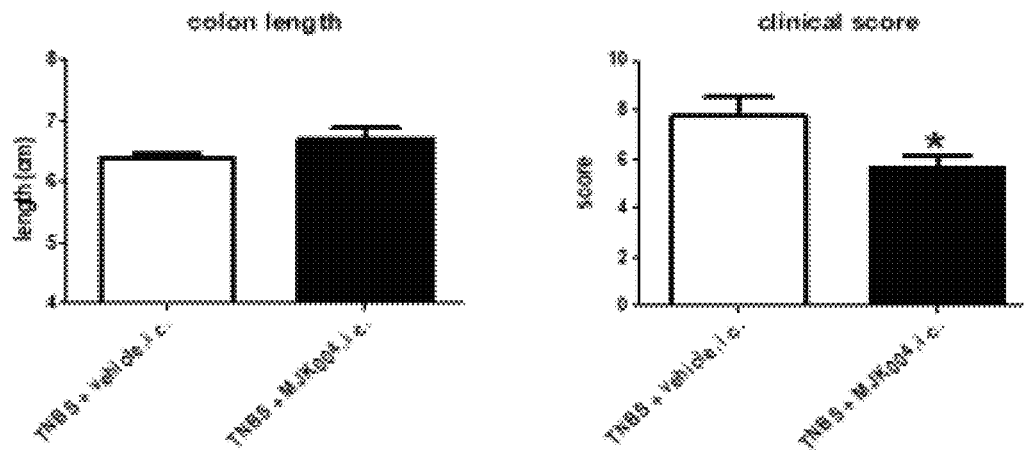
FIGS. 4A-4D show MJK-004, MJK-005, MJK-009 and MJK-011 administration yielded reduction in clinical scoring but did not alter colon length.
Figure 4B:
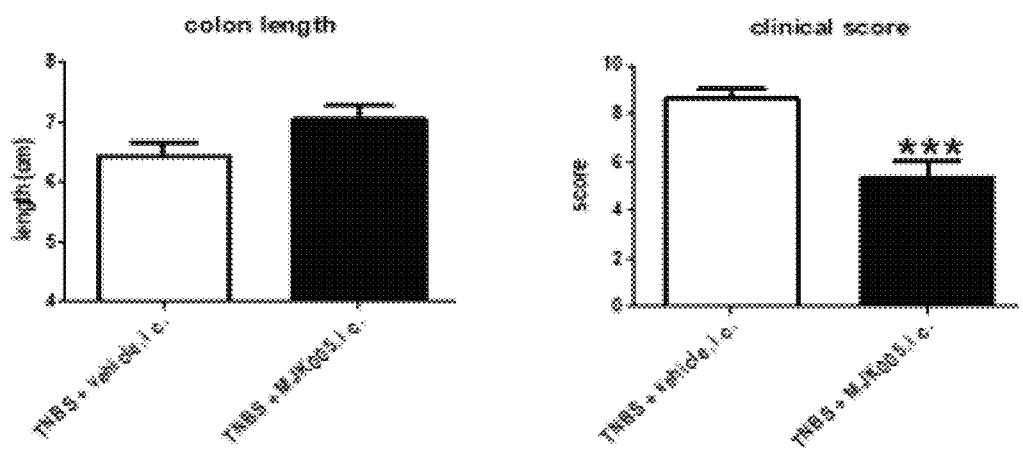
Figure 4C:
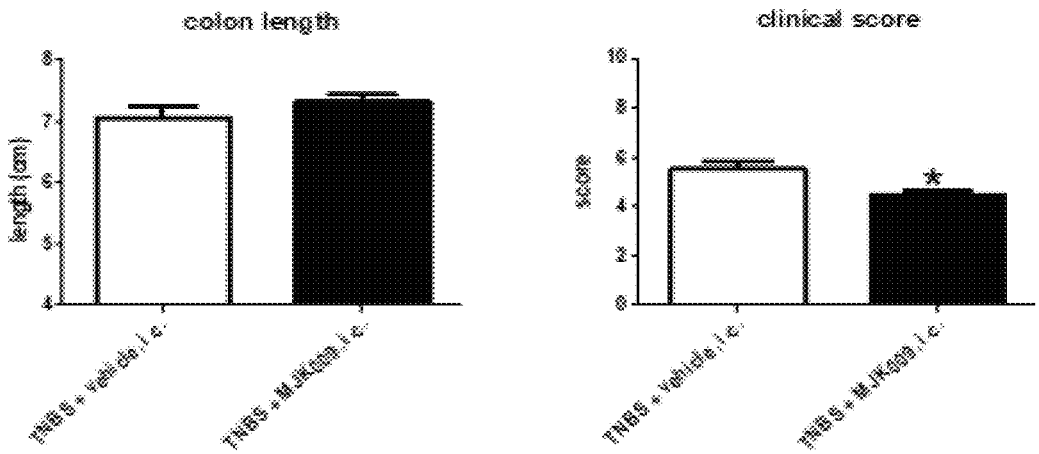
Figure 4D:
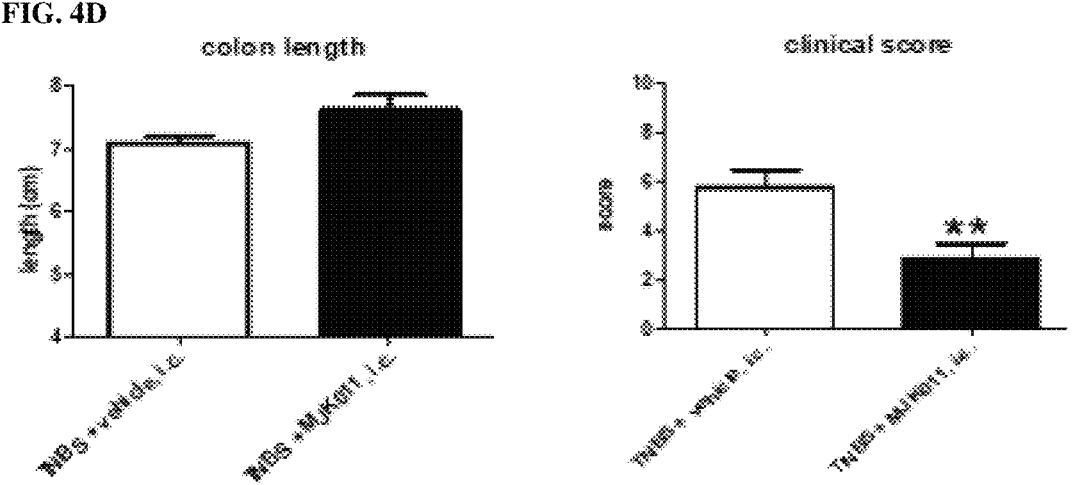
Figure 5A:
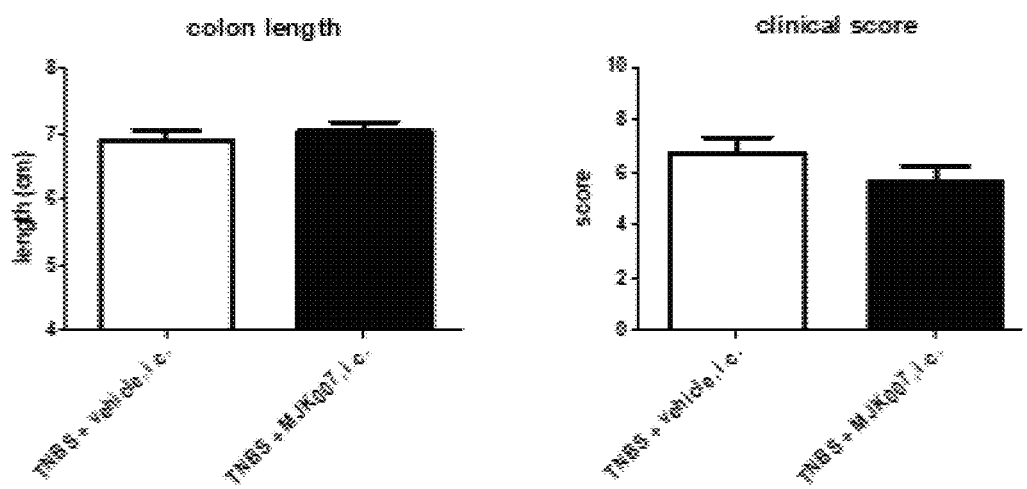
FIGS. 5A-5D show mice treated with MJK-007, MJK-010, MJK-012 or MJK-013 showed no significant differences from vehicle-treated mice in colon length or clinical scoring.
Figure 5B:
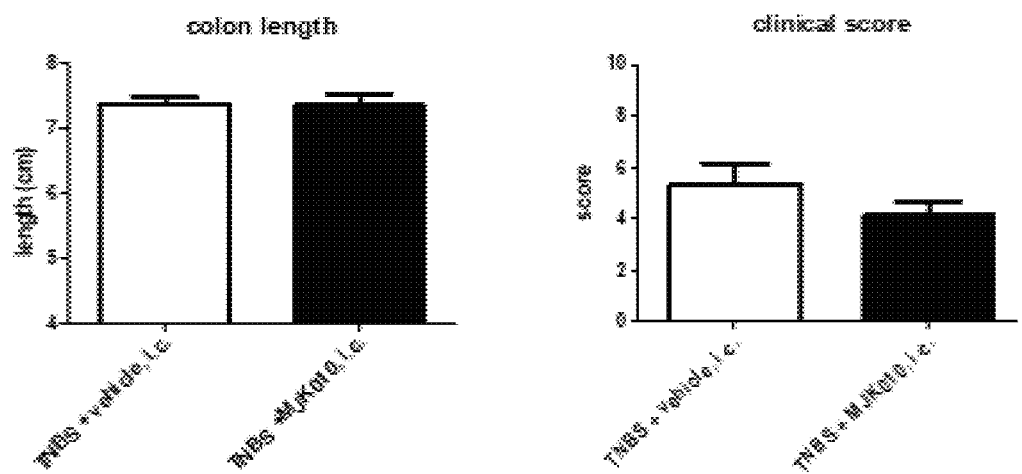
Figure 5C:
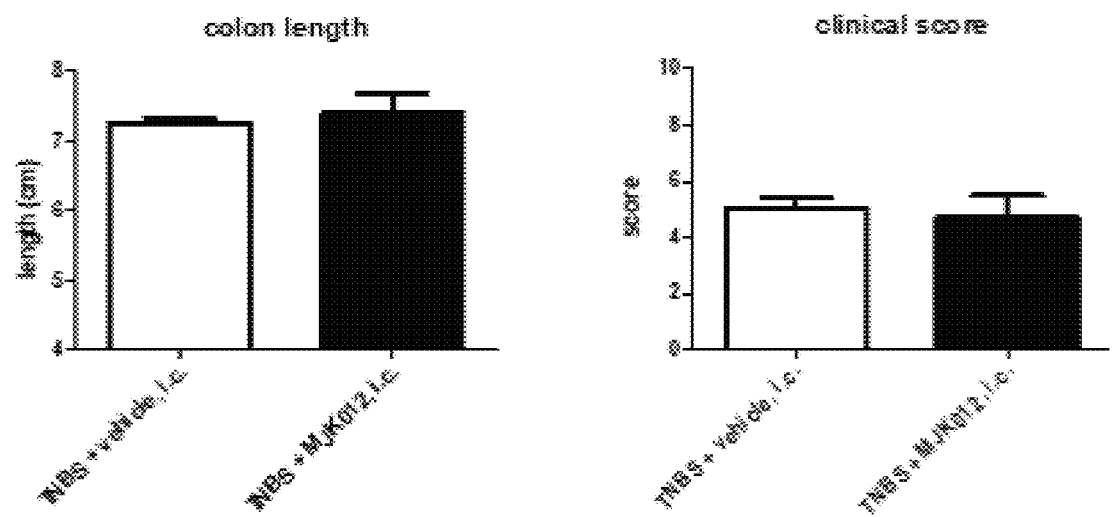
Figure 5D:
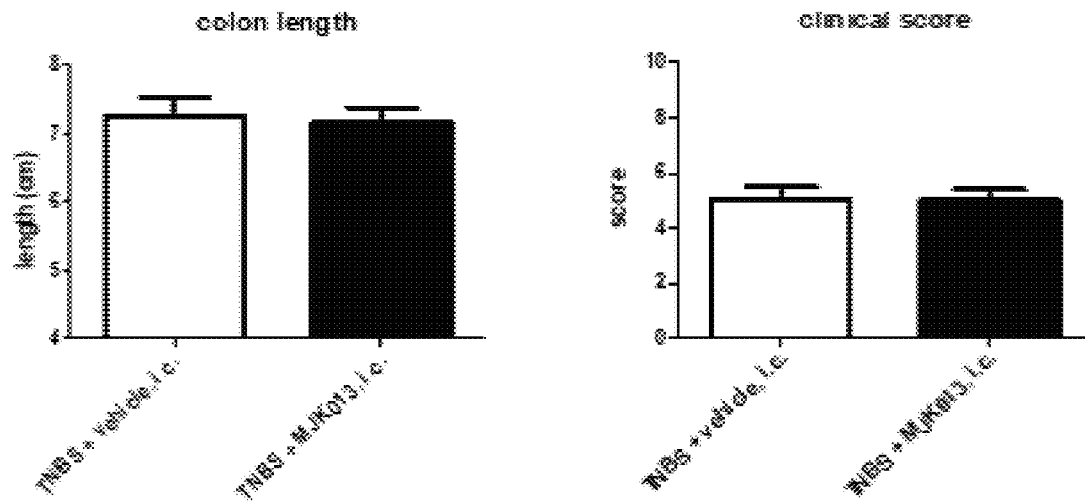

MJK-006 and MJK-008 have the best efficacy on suppressing colitis in vivo: Briefly, intracolonic administration of MJK-006 and MJK-008 had a substantial effect on suppressing TNBS-induced colitis in mice. Specifically, treatment with MJK-006 resulted in significant differences in colon length, clinical and histological scoring during TNBS colitis as compared to vehicle-treated mice (FIGS. 1A-1C). Representative histological sections from the colons of mice treated with MJK006 and their vehicle controls are shown, as well as photographs to illustrate the damage and ulceration observed in the colons of these animals and the extent of protection following intracolonic administration of MJK006 (FIG. 1D). Similarly, to MJK-006, MJK-008 was found to have significant effect in preserving colon length and decreasing the clinical and histological score (FIGS. 2A-2C) in comparison to untreated mice. Histological sections show that TNBS induces crypt damage, which was significantly restored after MJK-008 treatment (FIG. 2D). Mice treated with MJK-001, MJK-002 and MJK-003 showed statistical significance in the reduction of the clinical score and increase of colon length (FIGS. 3A-3C), however the results were much less impressive and significant in comparison to MJK-006 and MJK-008. Furthermore, MJK002 and MJK003 did not yield significant differences in histological scoring of colons from mice with TNBS colitis. MJK-004, MJK-005, MJK-009 and MJK-011 administration yielded reduction in clinical scoring but did not alter colon length (FIGS. 4A-4D). Overall, these four MJK compounds had moderate effects to suppress TNBS-colitis. Finally, mice treated with MJK-007, MJK-010, MJK-012 or MJK-013 showed no significant differences from vehicle-treated mice in colon length or clinical scoring (FIGS. 5A-5D). Taken together, MJK-006 and MJK-008 unexpectedly revealed very high efficacy on blocking TNBS-colitis and importantly reducing the damage and ulceration in these mice.

Solubility of MJK compounds: The development of an oral formulation for patients with auto-immune diseases, including Crohn's Disease, is preferential and less expensive, avoiding the need of hospitalization in comparison to the intracolonic (enema) administration. Thus, the water solubility and physical properties of the MJK compounds were examined. Based on this analysis, MJK-008 had the highest solubility together with MJK-009, while MJK-002 was more soluble than MJK-001 and MJK-003 (Table 1). On the other hand, MJK-006 and MJK-011 had the worst solubility. These findings suggest that the solubility of the compounds does not correlate with their effectiveness. MJK-008 is the highest soluble MJK compound.

TABLE 1

Solubility of MJK Compounds

| | score |
|---|---|
| MJK008 | ++++ |
| MJK009 | ++++ |
| MJK002 | +++ |
| MJK001 | ++ |
| MJK003 | ++ |
| MJK006 | + |
| MJK011 | + |

Figure 6A:
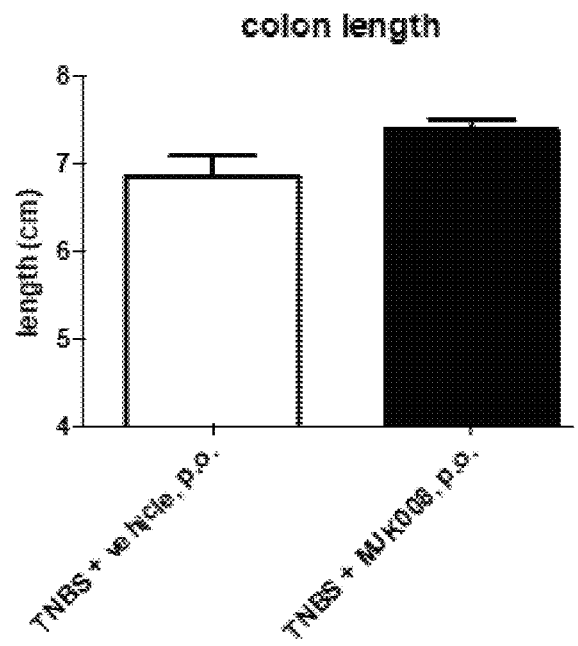
FIGS. 6A-6C shows that MJK-008 was highly efficient in reducing the clinical score, preserving colon length and decreasing the histology score.
Figure 6B:
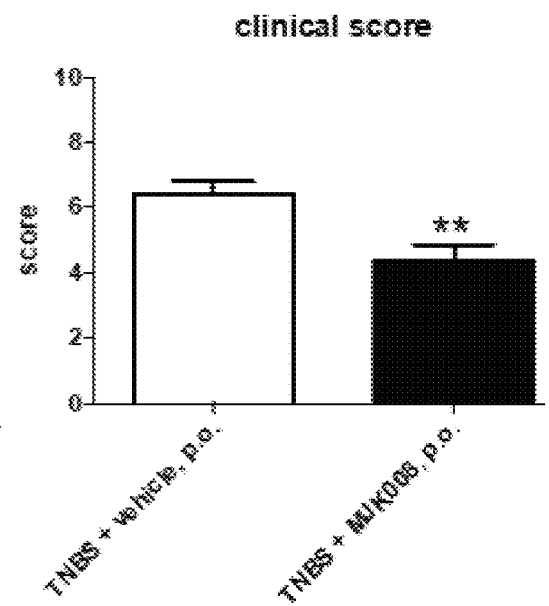
Figure 6C:
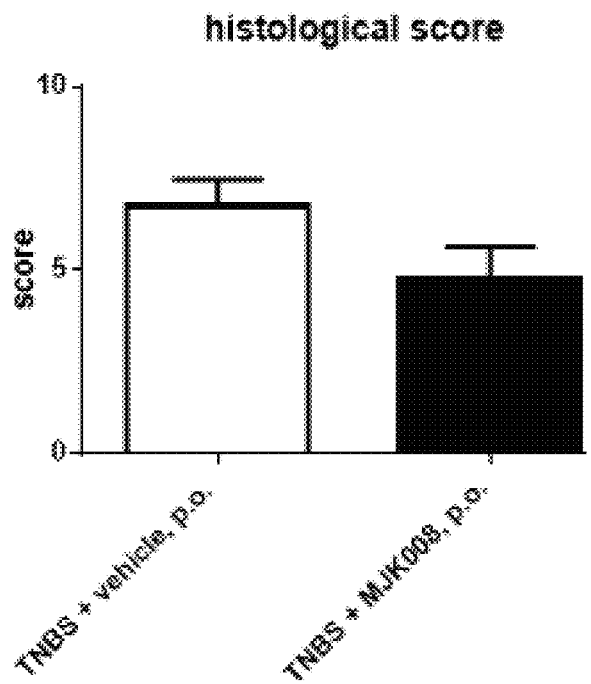

MJK-008 oral administration is effective to block experimental colitis: Based on the solubility and efficacy data in Table 2, MJK-008 has the best potential for the evaluation of its effectiveness when administered orally in mice with TNBS-colitis. Interestingly, MJK-008 was highly efficient in reducing the clinical score, preserving colon length and decreasing the histology score (FIGS. 6A-6C). Collectively, these findings show that MILK-008 has the potential to be used as an oral HDAC inhibitor in patients.

TABLE 2

Solubility and Efficacy Data

| | i.c. administration | | | |
|---|---|---|---|---|
| | colon length | clinical score | histological score | overall score |
| MJK006 | ♦♦ | ♦♦ | ♦♦♦ | +++ |
| MJK008 | ♦ | ♦♦ | ♦♦♦ | +++ |
| MJK002 | ♦ | ♦♦♦ | ns | ++ |
| MJK003 | ♦ | ♦♦ | ns | ++ |
| MJK001 | ♦♦ | ♦♦ | ♦♦ | ++ |
| MJK004 | ns | ♦♦ | − | + |
| MJK005 | ns | ♦♦♦ | − | + |
| MJK009 | ns | ♦ | − | + |
| MJK011 | ns | ♦♦♦ | − | + |
| MJK007 | ns | ns | − | − |
| MJK010 | ns | ns | − | − |
| MJK012 | ns | ns | − | − |
| MJK013 | ns | ns | − | − |

Figure 7:
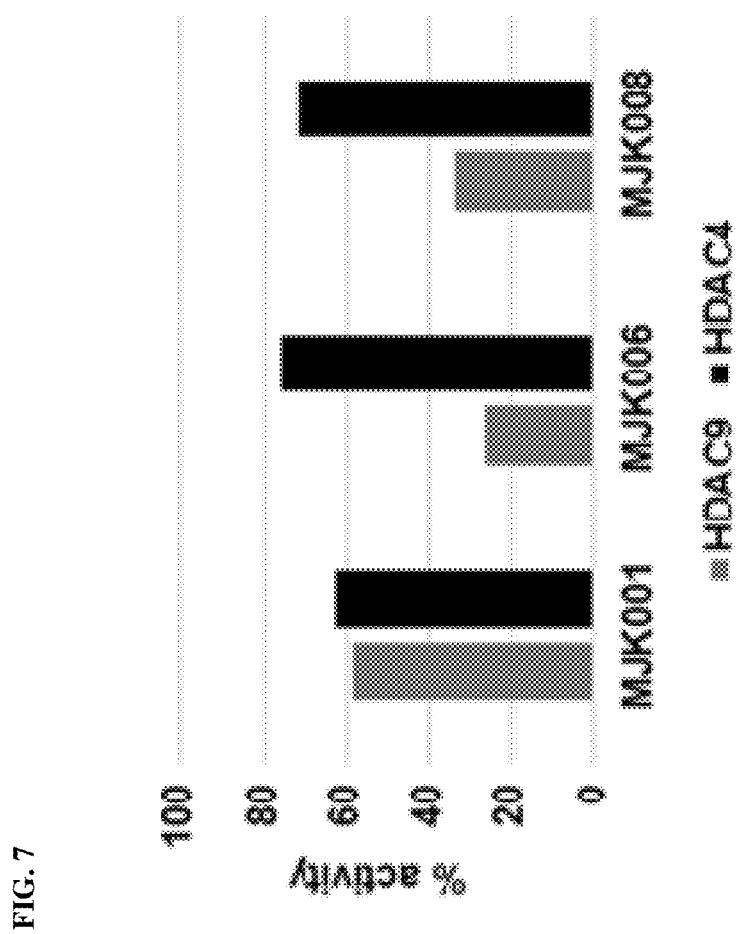
FIG. 7 shows that MJK-001 partially blocks both HDAC4 and HDAC9 isoforms, while MJK-006 and MJK-008 have high specificity for the HDAC9 isoform.

MJK-006 and MJK-008 target HDAC9 isoform: The identification of MJK-008 and MJK-006 as highly effective compounds for treatment of Crohn's Disease, based on the in vivo data, relative to the other compounds, led to an examination of their mechanism of action and specificity of targeting the HDAC Class IIA isoforms. This was based on the fact that MJK-001 partially blocks both HDAC4 and HDAC9 isoforms (FIG. 7). Interestingly, fluorogenic HDAC4 and HDAC9 assays revealed that both MJK-006 and MJK-008 have a significantly increased specificity of targeting the HDAC9 isoform and decreased HDAC4 specificity relative to MJK-001. These data propose that both MJK-006 and MJK-008 are HDAC9 isoform targeting compounds.

Figure 8:
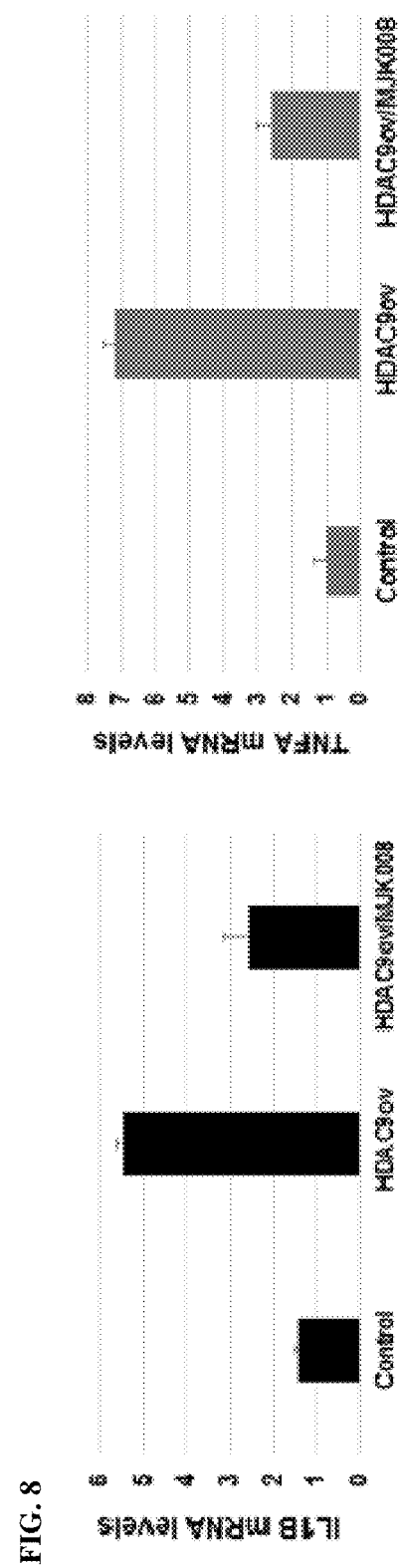
FIG. 8 shows that HDAC9 overexpression results in substantial increase in IL1B and TNFA mRNA levels.

MJK-008 regulates inflammation through HDAC9: To further explore the relationship between MJK-008 and HDAC9, the effects of MJK-008 on IL1B and TNFA expression in HDAC9-overexpressing NCM356 colonocytes were examined. HDAC9 overexpression results in substantial increase in IL1B and TNFA mRNA levels (FIG. 8). Interestingly, MJK-008 treatment in the HDAC9-overexpressing NCM356 cells reduced substantially the inflammatory response, through suppression of IL1B and TNFA, both key pro-inflammatory molecules, involved in the pathogenesis of auto-immune diseases, including Crohn's Disease, Ulcerative Colitis, Lupus and Rheumatoid Arthritis. These findings reveal that MJK-008 suppresses the inflammatory response, primarily through regulation of HDAC9 expression.

HDAC9-inflammatory gene/drug network: Furthermore, chromatin immunoprecipitation followed by sequencing (ChIP-seq) in HDAC9-overexpressing NCM356 cells was performed and it was found that HDAC9 directly regulates 1339 gene targets. Gene network analysis revealed that the main network regulated by HDAC9 includes 21 IBD SNP loci. Specifically, it targets IL23, IL6, TNFA, IL1B, IL10, CXCL2 and IL8, which all consist drug targets for auto-immune diseases, including Crohn's Disease, Ulcerative Colitis, Lupus and Rheumatoid Arthritis. The identification of 21 gene loci involved in IBD pathogenesis and their regulation through HDAC9 provides a rationale for dramatic effects of MJK-008 on suppressing the inflammatory response.

MJK-001 effects on a cancer cell line panel: The effects of MJK-001 (20 uM) on cancer cell growth was evaluated in 9 cancer cell lines, consisting of bladder, colon, lung, prostate and pancreatic cancer cell lines. Cell growth was measured on day 5. Bladder cancer cell lines (RT-112, 5637) were more responsive to MJK-001 treatment, followed by the colon and pancreatic cancer cell lines shown in Table 3. These data suggest a potential use of MJK-001 on bladder cancer, however it is important to mention that the MJK-001 effects were identified by using a very high concentration (20 uM), thus having a small potential to be further evaluated.

TABLE 3

The Effects of MJK-001 (20 uM) on Cancer Cell Growth

| 20 uM − MJK001 Cancer type | Cell Lines | % growth inhibition |
|---|---|---|
| Bladder | RT112 | 51.02 |
| Bladder | 5637 | 42.06 |
| Colon | SW480 | 58.44 |
| Colon | HT-29 | 19.67 |
| Lung | NCI-460 | 3.42 |
| Lung | NCI-1975 | 11.82 |
| Prostate | PC-3 | 26.81 |
| Pancreas | MIA PaCa-2 | 0.00 |
| Pancreas | CAPAN-2 | 42.68 |

MJK-004 efficacy on bladder cancer cell growth and colony-formation ability: Based on the above findings, the MJK compounds were examined to determine if they had substantially better efficacy than MJK-001 to suppress bladder cancer cell growth by calculating the IC50 values. Interestingly, MJK-004 was found to have a major effect on blocking the growth of RT-112 and UMUC9 bladder cancer cell lines, having the lowest IC50 values in comparison to the other MJK compounds shown in Table 4. Surprisingly, while MJK-004 had the highest efficacy, MJK-006 and MJK-008, identified above as the top anti-inflammatory compounds, did not have any effect. Additional examination of MJK-004 effectiveness on bladder cancer cell growth revealed, low IC50 values in BC3C (5.847 uM), EJ28 (6.623 uM) and 5637 (7.582 uM) bladder cancer cell lines relative to MJK-006 (36.37 uM, 352.3 uM, 1738 uM respectively).

Figure 9:
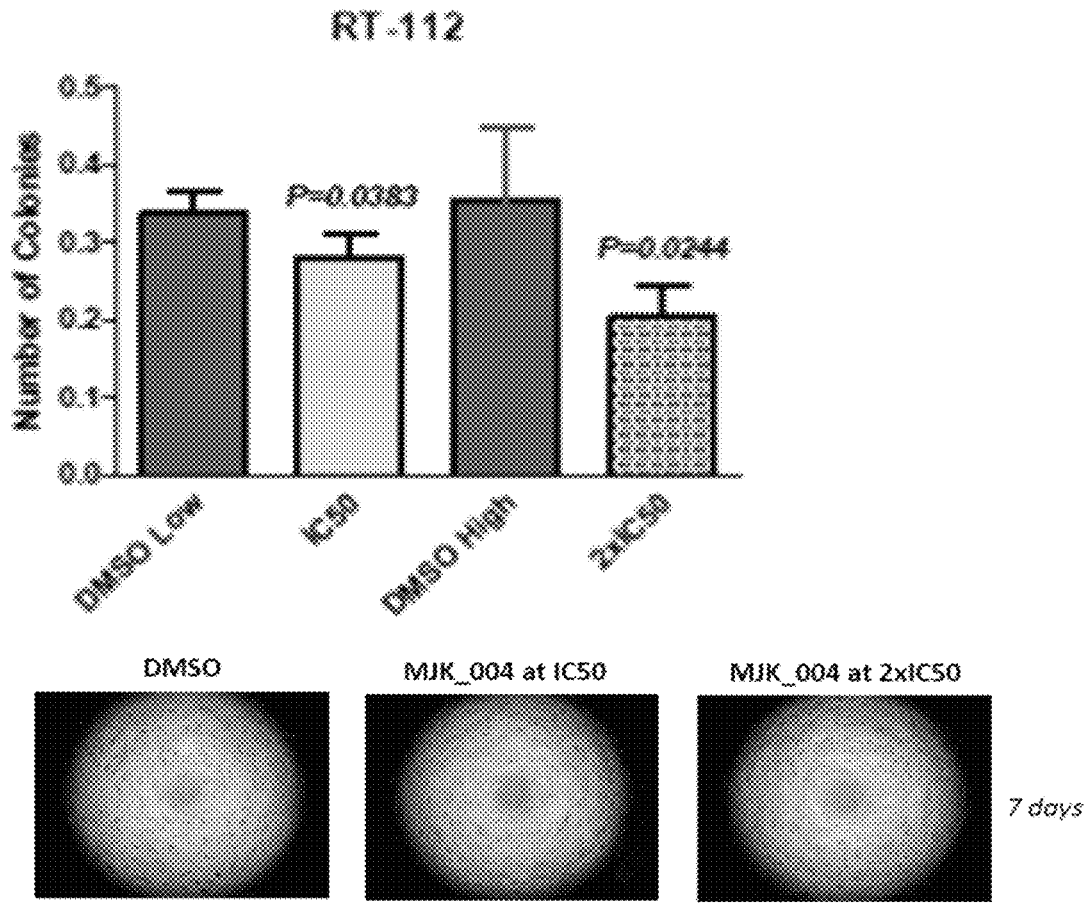
FIG. 9 shows that MJK-004 reduced significantly the ability of RT-112 bladder cancer cells to form colonies in soft agar.

In addition, MJK-004 reduced significantly, the ability of RT-112 bladder cancer cells to form colonies in soft agar (FIG. 9). Taken together, these data surprisingly revealed the high efficacy of MJK-004 to suppress bladder cancer cell growth.

TABLE 4

The Efficacy of Suppressing Bladder Cancer Cell Growth

| Cancer Cell Line | IC50 (uM) values MJK001 | MJK004 | MJK006 | MJK008 |
|---|---|---|---|---|
| RT-112 | 9.152 | 2.374 | 38.28 | ns |
| UMUC9 | 7.099 | 3.971 | 19.77 | ns |

Figure 10:
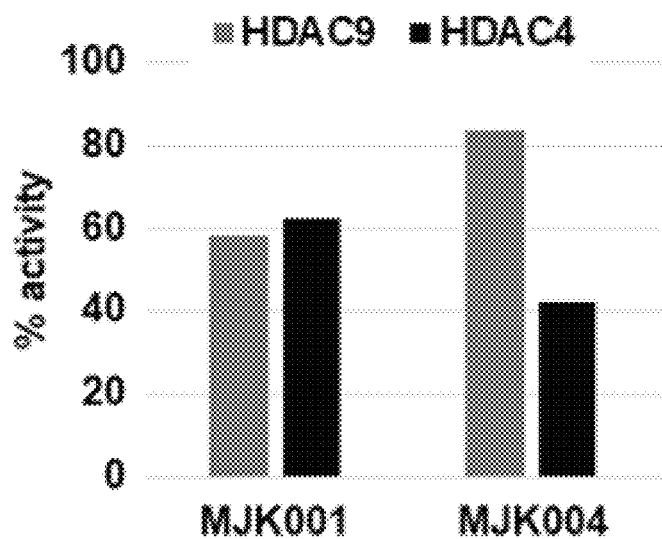
FIG. 10 shows that MJK-004 has high specificity for HDAC4 and very low activity against HDAC9.

MJK-004 targets HDAC4 isoform: To identify MJK-004 HDAC isoform activity, HDAC4 and HDAC9 fluorogenic activity assays were performed. Interestingly, MJK-004 showed high specificity for HDAC4 and very low activity against HDAC9 (FIG. 10), which is totally opposite regarding the MJK-006 and MJK-008 specificity for HDAC9 (FIG. 7).

MJK-004 molecular signature in bladder cancer: To examine the genes and signaling pathways affected by MJK-004 treatment in bladder cancer, RNA-sequencing analysis was performed in RT-112 and UMUC9 cell lines. Gene network analysis based on the differentially expressed genes revealed ERK, NURP1 and VEGF as central regulators of MJK-004 effects in RT-112 cells. Similar analysis showed that GPCR, IFN, S100A8, FOXA2, PPARGC1 and IL1 are central regulators of the networks regulated by MJK-004 in UMUC9 bladder cancer cells. Overall, these findings suggest that MJK-004 regulates kinase and metabolic signaling pathways in bladder cancer cells.

Figure 11:
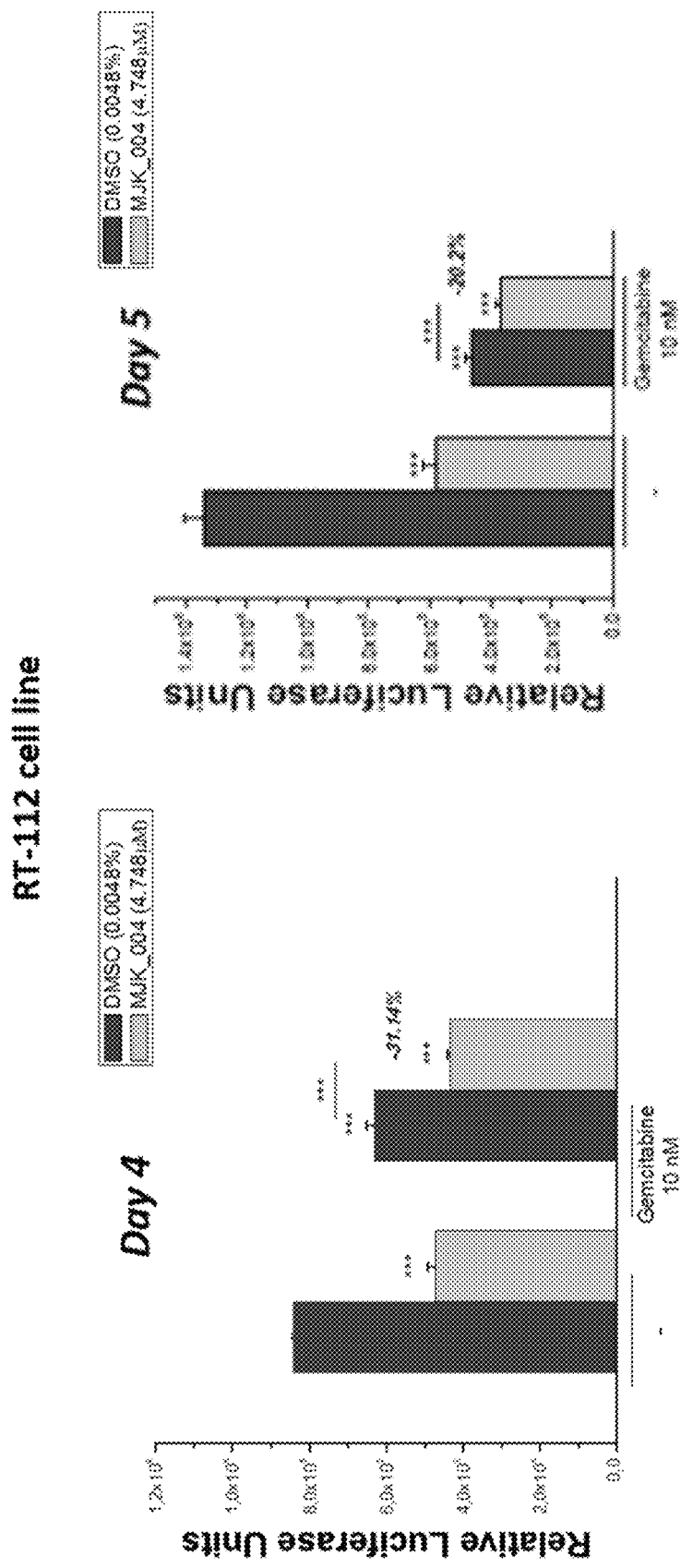
FIG. 11 shows MJK-004 suppressed bladder cancer growth in both cell lines as a monotherapy. MJK-004 combination with gemcitabine increased gemcitabine's efficacy in RT-112 and UMUC9 bladder cancer cells.
Figure 11:
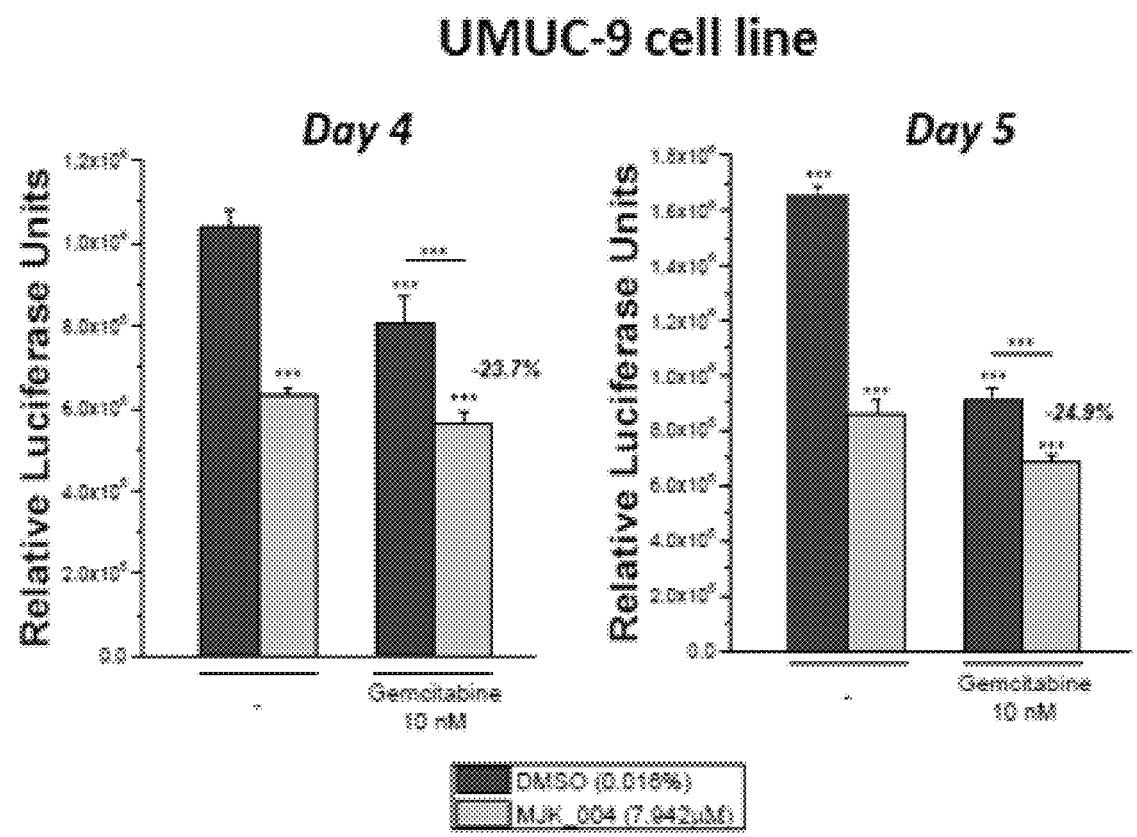

MJK-004 and chemotherapy have synergistic effects on bladder cancer: The effects of MJK-004 treatment as a monotherapy or in combination with gemcitabine chemotherapy were evaluated. RT-112 and UMUC9 bladder cancer cells were treated with MJK-004 and/or gemcitabine (10 nM—low concentration) and cell growth was evaluated on days 4 & 5 (FIG. 11). Interestingly, MJK-004 suppressed bladder cancer growth in both cell lines as a monotherapy. MJK-004 combination with gemcitabine increased gemcitabine's efficacy in RT-112 and UMUC9 bladder cancer cells. These findings suggest that MJK-004 is highly effective to suppress bladder cancer cell growth in combination with low concentration of gemcitabine chemotherapy.

The synthesized series of MJK chemical compounds have increased specificity for HDAC9 or HDAC4 isoforms. Interestingly, MJK-008 and MJK-006 are highly effective in blocking inflammation in vitro and in vivo through regulation of HDAC9, while they did not have any effect on cancer cell growth. On the other hand, MJK-004 is highly efficient in blocking bladder cancer cell growth through regulation of HDAC4 isoform. MJK-006 and MJK-008 compounds have the potential to be developed as therapeutics for Crohn's Disease and other auto-immune diseases. MJK-004 compound has the potential to developed as a therapeutic against bladder cancer in combination with chemotherapy. The findings for MJK-006, -008 and -004 compounds are shown in Table 5.

TABLE 5

The Activity of MJK-006, -008 and -004 Compounds

| Compound | HDAC4 | Bladderca | HDAC9 | Crohn's |
|---|---|---|---|---|
| 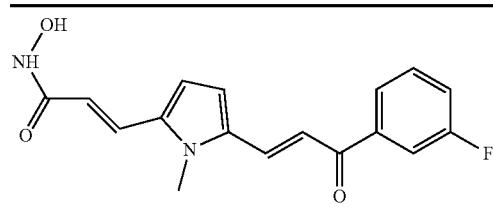 MJK001 | ++ | ++ | ++ | ++ |
| 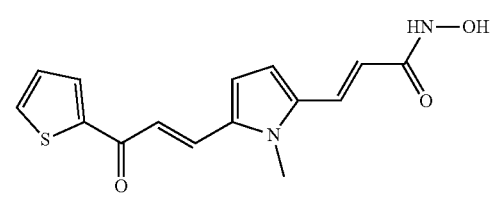 MJK004 | +++ | ++++ | + | + |
| 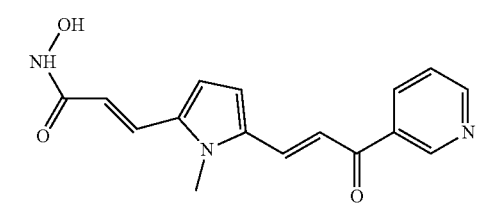 MJK006 | + | + | ++++ | ++++ |

TABLE 5-continued

The Activity of MJK-006, -008 and -004 Compounds

| Compound | HDAC4 | Bladderca | HDAC9 | Crohn's |
|---|---|---|---|---|
| MJK008 | + | + | ++++ | ++++ |

REFERENCES (1) Mai, A.; Massa, S.; Pezzi, R.; Simeoni, S.; Rotili, D.; Nebbioso, A.; Scognamiglio, A.; Altucci, L.; Loidl, P.; Brosch, G. *J Med. Chem.* 2005, 48, 3344-3353.
(2) Fleming, C. L.; Ashton, T. D.; Gaur, V.; McGee, S. L.; Pfeffer, F. M. *J. Med. Chem.* 2014, 57, 1132-1135.
(3) Hong, B. T.; Chen, C. L.; Fang, J. M.; Tsai, K. C.; Wang, S. Y.; Huang, W. I.; Cheng, Y. S. E.; Wong, C. H. *Bioorg. Med. Chem.* 2014, 22, 6647-6654.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of formula I, or a pharmaceutically acceptable salt thereof:

(I)

wherein:
R$^1$ is pyrrolyl, pyridinyl, or pyrazinyl, each of which is optionally substituted with one or more groups selected from alkyl and halo; and
R$^2$ is alkyl.

2. The compound of claim 1, wherein R$^1$ is pyrrolyl and is optionally substituted at the N-position with alkyl.

3. The compound of claim 1, wherein R$^1$ is pyridinyl or pyrazinyl, each of which is optionally substituted.

4. The compound of claim 3, wherein R$^1$ is optionally substituted pyridinyl.

5. The compound of claim 1, wherein: R$^2$ is methyl.

6. A pharmaceutical composition comprising a compound of claim 1 and a pharmaceutically acceptable excipient.

7. The compound of claim 1, wherein R$^1$ is pyridiny-3-yl.

8. The compound of claim 1, wherein the compound is or a pharmaceutically acceptable salt thereof.

9. The compound of claim 8, wherein the compound is

10. The compound of claim 8, wherein the compound is

11. The compound of claim 8, wherein the compound is

* * * * *